United States Patent [19]

Haber et al.

[11] Patent Number: 5,298,023
[45] Date of Patent: Mar. 29, 1994

[54] MULTIPLE PHARMACEUTICAL DISPENSER WITH ACCUMULATOR

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 949,265

[22] Filed: Sep. 22, 1992

Related U.S. Application Data

[63] Continuation-in-part of Ser. No. 718,398, Jun. 21, 1991, Pat. No. 5,199,949, which is a continuation-in-part of Ser. No. 667,319, Mar. 8, 1991, Pat. No. 5,147,323, and a continuation-in-part of Ser. No. 668,278, Mar. 8, 1991.

[51] Int. Cl.⁵ .................. A61M 37/00; A61M 5/00
[52] U.S. Cl. ........................... 604/90; 604/191; 604/232; 604/211
[58] Field of Search ............ 604/72, 82, 86-90, 604/187, 191, 151, 152, 232-235, 207, 208, 211, 83

[56] References Cited

U.S. PATENT DOCUMENTS

| | | |
|---|---|---|
| 1,557,836 | 10/1925 | Hein . |
| 3,659,587 | 5/1972 | Baldwin . |
| 3,696,806 | 10/1972 | Sausse . |
| 4,109,653 | 8/1978 | Kozum et al. . |
| 4,592,745 | 6/1986 | Rex et al. ............ 604/211 |
| 4,738,660 | 4/1988 | Lucas . |
| 4,755,109 | 7/1988 | Sarnoff et al. . |
| 4,795,441 | 1/1989 | Bhatt . |
| 4,902,281 | 2/1990 | Avoy . |
| 4,936,833 | 6/1990 | Sams ................ 604/232 |
| 5,067,948 | 11/1991 | Haber et al. . |
| 5,078,691 | 1/1992 | Hamacher . |
| 5,226,895 | 7/1993 | Harris ............... 604/208 |
| 5,226,896 | 7/1993 | Harris ............... 604/211 |

Primary Examiner—John D. Yasko
Assistant Examiner—Adam J. Cermak
Attorney, Agent, or Firm—Townsend & Townsend Khourie & Crew

[57] ABSTRACT

A multiple pharmaceutical syringe (2, 160, 402), especially useful for use in dispensing insulin, includes a body (4, 162, 404) housing first and second pharmaceutical-filled cartridges (30, 32; 182, 184; 478, 480). The cartridges are of the type with a septum (36, 190, 484) at one end and a piston (42, 48; 224, 225; 562, 564) at the other end with the liquid pharmaceutical (46, 48; 226, 228; 534, 536) between the two. The body also defines an accumulator chamber (10, 202, 654) within which an accumulator piston (26, 238, 464) is slidably mounted. The cartridge interiors are connected by a flow path (70, 752) to the accumulator chamber. Pressing on the cartridge pistons forces desired amounts of the liquids from the cartridge into the accumulator chamber. The mixed pharmaceutical is dispensed by driving the accumulator piston.

28 Claims, 37 Drawing Sheets

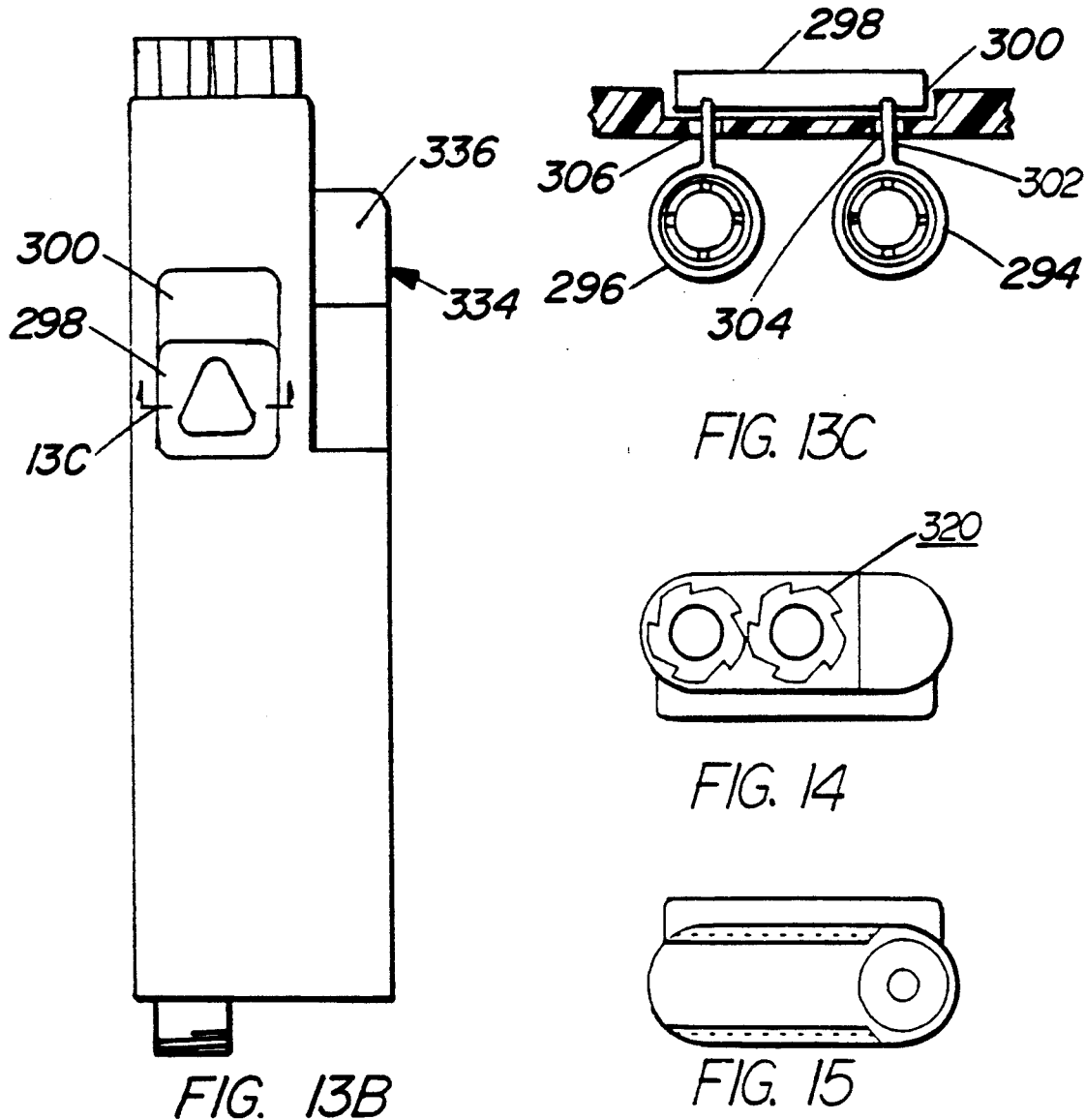

MULTIPLE PHARMACEUTICAL DISPENSER WITH ACCUMULATOR

CROSS REFERENCE TO RELATED APPLICATIONS

This is a continuation-in-part of U.S. patent application No. 07/718,398 titled MULTIPLE PHARMACEUTICAL SYRINGE, filed Jun. 21, 1991, now U.S. Pat. No. 5,199,949, which is a continuation-in-part of both U.S. patent application No. 07/667,319, titled MULTIPLE CARTRIDGE SYRINGE, now U.S. Pat. No. 5,147,323, and U.S. patent application No. 07/668,278, titled MULTIPHARMACEUTICAL SYRINGE, both of which were filed on Mar. 8, 1991, the disclosures of all three being incorporated by reference for all purposes.

BACKGROUND OF THE INVENTION

Therapeutic insulin is of three basic types: fast-acting, intermediate-acting and long-acting. Insulin users often use a combination of two types of insulin depending on the user's blood sugar level, the time of day, nourishment intake, and expected activity. For example, insulin injected at the beginning of an active day may have more of the fast-acting insulin, while the insulin injection given at the end of the day before going to bed would likely have more intermediate- or long-acting insulin.

One of the problems with conventional insulin syringes is that they are designed to inject only one type of insulin, not a combination. Although insulin can be obtained as a mixture of the two types, the mixtures are generally a preset combination, such as 70% intermediate-acting and 30% fast-acting. Thus, the prior art limits the insulin user to a set mixture of the two insulins or the need to make two separate injections.

SUMMARY OF THE INVENTION

The present invention is directed to a pharmaceutical dispenser, such as a syringe, which preferably uses two or more conventional pharmaceutical cartridges to allow the user to deliver desired amounts and proportions of each during a single pharmaceutical delivery event, such as a single injection, from a common accumulator chamber. This permits, for example, an insulin user to select the amounts and proportions of two types of insulin delivered with a single injection.

The multiple cartridge syringe includes a body housing first and second pharmaceutical-filled containers, preferably cartridges. The cartridges preferably are of the type with a septum at one end, an exposed piston at the other and the liquid pharmaceutical between the two. The body also houses an accumulator chamber within which an accumulator piston is slidably contained. In one embodiment the proximal end of the body is open to provide access to the three pistons by a single stem. In other embodiments separate drive stems are used for each cartridge piston and for the accumulator piston.

The cartridge septums are preferably each pierced by hollow spikes. The hollow spikes are connected to a flow path which opens into the distal end of the accumulator chamber. Check valves are preferably used, typically at the distal ends of the spikes, to allow the pharmaceutical within each cartridge to flow out of the cartridge through the spike but not the reverse.

Pressing on the piston within a cartridge causes the pharmaceutical within the cartridge to flow through the spike, through the check valve, along the flow path and into the accumulator chamber. The pressure and increasing volume of the liquid within the accumulator chamber forces the accumulator piston away from the distal end of the accumulator chamber towards the proximal end of the body. The cartridge pistons are each acted on until the desired amounts of both liquid pharmaceuticals have been forced into the accumulator chamber and mixed therein.

When a hollow needle is used to disperse the mixed pharmaceutical from the accumulator chamber, the needle is then fluidly coupled to the accumulator chamber. In one embodiment this is accomplished by moving a needle assembly from its normally stored or retracted position to an extended position using pivotal or linear motion. This causes the distal end of the accumulator chamber to be fluidly coupled to the hollow needle. Pressing on the stem connected to the accumulator piston forces the newly-mixed liquids within the accumulator chamber through the hollow needle. Once the injection has been given, the needle assembly is moved back to its retracted position. This not only moves the needle to a safe position shielded by the body, but also seals the needle from the accumulator chamber.

A single stem can be used to drive each of the pistons one-at-a-time. With this embodiment the stem can be retained by an end cap slidably mounted to the proximal end of the body. The end cap guides the stem as it pushes against the various pistons. After withdrawing the piston from the body, the end cap can be slid laterally to align the distal end of stem with a different piston.

A primary feature of the invention is that it permits a single injection of selected amounts and proportions of two or more liquid pharmaceuticals using a simple and compact syringe. In addition, the invention is designed to be usable with conventional pharmaceutical cartridges for reduced cost and enhanced flexibility. An insulin user is provided a flexible, convenient and compact syringe by which any desired proportion of insulins can be administered with a single injection.

The accumulator piston can be made with a collapsible sterility skirt connected to the proximal end of the accumulator chamber. This will protect the sterility of the accumulator chamber during use and between uses.

The accumulator chamber can be sized to house substantially the entire stem or stems when the syringe is not being used. This, plus an in-line arrangement of the cartridges and the accumulator chamber, allows the syringe to be quite compact and yet a relatively sturdy package.

The preferred configuration of the syringe reduces or eliminates the stigma of abnormality created by the use of conventional hypodermic syringes and pharmaceutical vials.

The invention can be carried out using a replaceable manifold/accumulator assembly by which the accumulator and the check valves and flow paths connecting the interiors of the cartridges to the accumulator chamber are replaceable as a unit. This permits most of the syringe to be reusable, thus reducing cost for the user, while enhancing sterility. In a preferred embodiment, this is accomplished by mounting the cartridges to the replaceable manifold/accumulator assembly, the combination being mounted to the dispenser body.

Although the syringes shown are intended to be reusable, they could easily be modified to be disposable by the user. One way to do so for the embodiment using a single stem would be to prevent removal of the end cap and thus prevent removal of one or both of the spent pharmaceutical cartridges.

Another feature of the invention involves a provision of measured metering of the pharmaceuticals. This preferably accomplished using a preferably externally threaded stem driven by a hollow stem driver having internal threads at one end, the threaded stem driver being rotatable by the user. The threaded stem driver is preferably ratcheted and detented to provide audible and tactile indications of the amount of the pharmaceutical being dispensed from each cartridge. The invention can also be carried out using a linear ratchet drive mechanism whereby the stem is driven by the reciprocal linear movement of a ratchet stem driver, as opposed to the rotary motion of a threaded stem driver.

To reposition the stem relative to the stem driver, which is necessary when changing cartridges, a locking collar is preferably used to selectively secure the preferably externally threaded stem to the preferably internally threaded end of the stem driver. In this way, by moving the locking collar the end of the stem driver dilates so that threads disengage to permit the stem to be repositioned within the stem driver. In one embodiment, the stems are automatically repositioned within the dispenser by the simple process of inserting a manifold/cartridge/ accumulator assembly into the body of the dispenser.

The present invention can also be carried out using a visually distinct display to visually indicate the movement of the plungers within the pharmaceutical cartridges, thus indicating the amount of pharmaceutical dispensed from each. This is preferably accomplished using a pick-up which senses the rotation of the stem driver and advances a visual indicator, such as a continuous ribbon loop, in a manner which magnifies the movement of the piston. That is, if the piston moves 0.84 millimeter to dispense one unit of medicine, the indicator ribbon loop may move two or more times that distance. This magnification of distance is especially helpful for those users with poor eyesight.

Another feature of the invention relates to the construction of the threaded stem driver. To allow the user to easily grasp the proximal end of the threaded stem driver, it is provided with a telescoping knob which extends proximally at the push of a button. In addition, the dispenser preferably is constructed to cause the dose indicators to automatically return to an initial or zero reading at the end of each dispensing stroke of the accumulator stem.

Other features and advantages of the invention will appear from the following description in which the preferred embodiments have been set forth in detail in conjunction with the accompanying drawings.

BRIEF DESCRIPTION OF THE DRAWINGS

FIGS. 13, 14 and 15 are side, proximal end and distal end views of the syringe of FIG. 12 respectively, the accumulator chamber thumb driver shown pivoted to the use position in phantom in FIG. 13;

FIGS. 13A and 13B are front and rear plan views of the syringe of FIG. 12;

FIG. 13C is a partial cross-sectional view of the button taken along line 13C of FIG. 13B;

FIG. 34B is similar to FIG. 34A, but illustrates the counterclockwise pivoting of the rocker cam follower following the depression of the proximal end of the accumulator stem assembly at the end of a delivery stroke, thus compressing the accumulator spring and causing the cam contact portion of the rocker cam follower to ride up on the rocker arm cam surface of the accumulator guide sleeve, thus lifting the proximal end of the display frame and window therewith away from the dose screws so to disengage the teeth of the followers from the external indicator threads of the dose screws to permit the elastic band connected to each follower to return the indicator ribbon to its initial or zero reading;

DETAILED DESCRIPTION OF THE PREFERRED EMBODIMENTS

Figure 4:
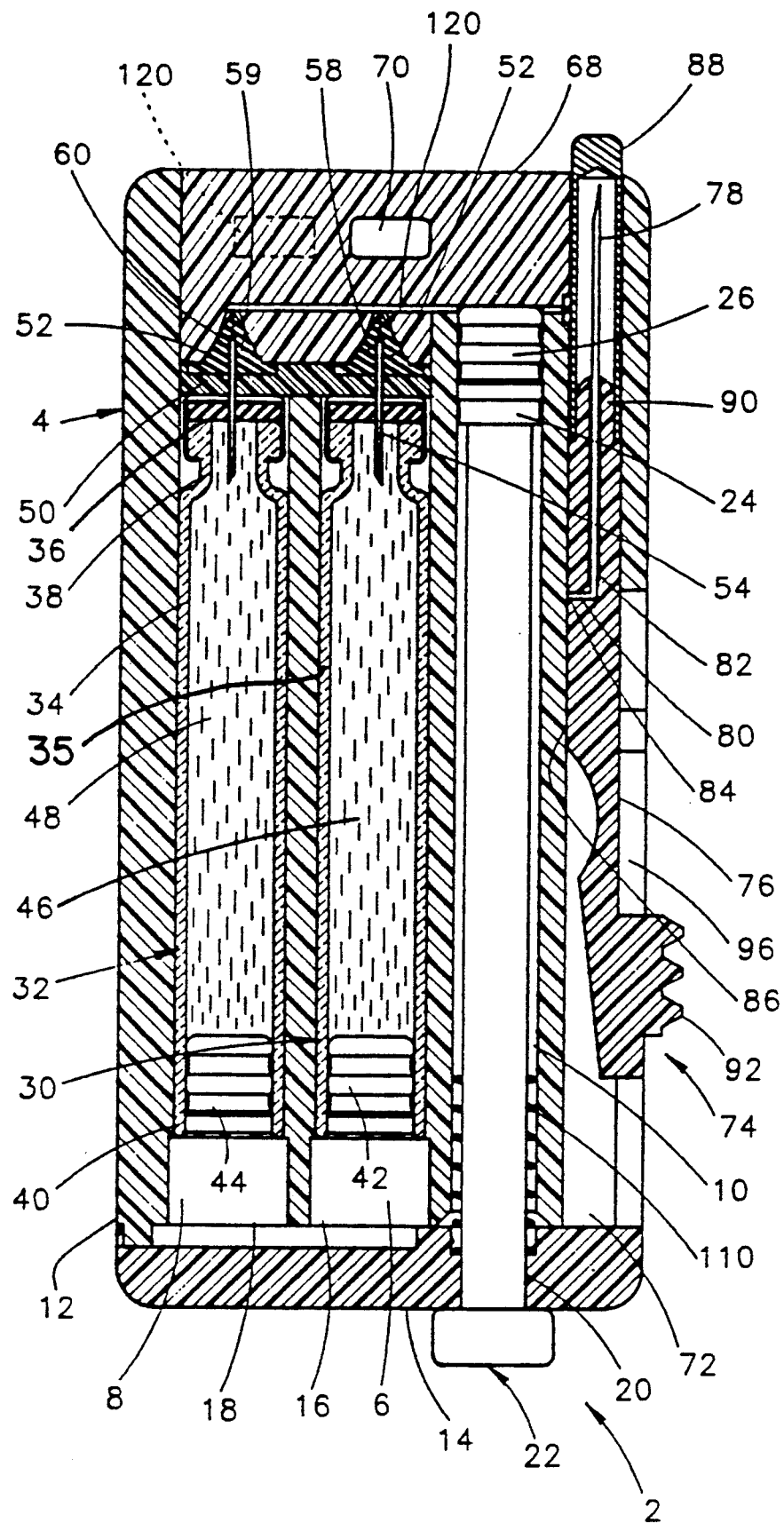
FIG. 4 is a cross-sectional view taken along line 4—4 of FIG. 2.

Referring the reader to FIGS. 1–4, a multiple cartridge syringe 2 is shown to include a body 4 defining first and second chambers 6, 8 and an accumulator chamber 10. Body 4 is made of a clear, pharmaceutically compatible plastic, such as polypropylene or acrylic. A proximal end 12 of body 4 is covered by a sliding end cap 14, thus covering the opened proximal ends 16, 18 of chambers 6, 8. End cap 14 has an opening 20 through which a stem 22 passes. As shown in FIG. 4, the distal end 24 of stem 22 is normally positioned adjacent a piston 26 mounted within accumulator chamber 10 at a distal end 28, see FIG. 5, of chamber 10.

Chambers 6, 8 are sized for receipt of first and second conventional pharmaceutical cartridges 30, 32. Cartridges 30, 32 each include a barrel 34, 35 having a pierceable septum 36 at a far end 38 and an opened near end 40. First and second cartridges 6, 8 include first and second pistons 42, 44 and contain first and second liquid pharmaceuticals 46, 48 between septums 36 and pistons 42, 44.

Figure 7:
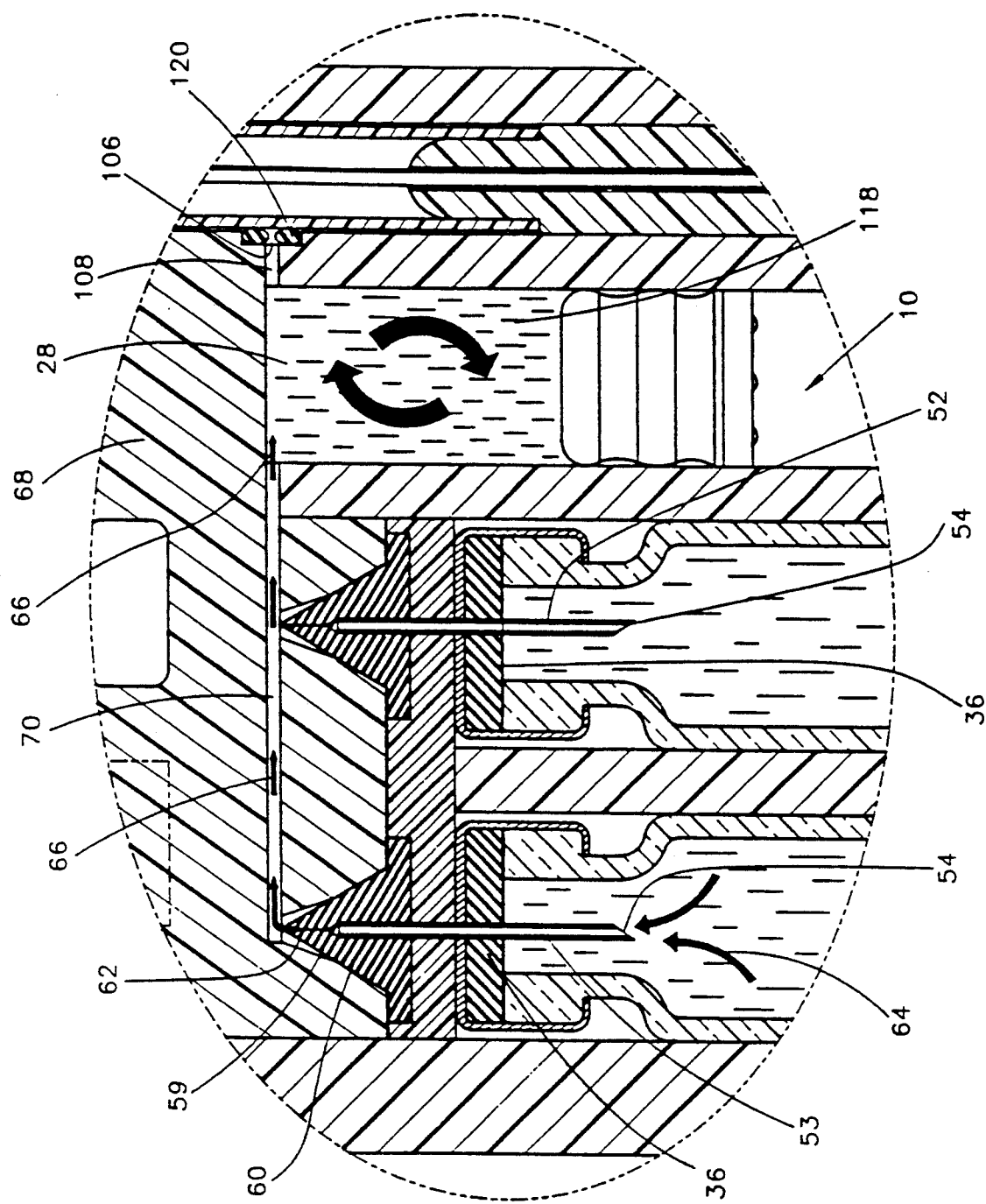
FIG. 7 is an enlarged view of a portion of the syringe of FIG. 6 taken along line 7—7.

The far ends 38 of first and second cartridges 30, 32 rest against a check valve support plate 50. Hollow spikes 52, 53 (see FIG. 7) are mounted to and pass through support plate 50. Spikes 52, 53 have sharpened ends 54 which pierce septums 36 when cartridges 30, 32 are inserted into first and second chambers 6, 8. Slit conical check valves 58, 59, shown best in FIG. 7, are mounted to the outer ends 60 of spikes 52. Check valves 58, 59 have slits 62 which permit fluid to flow in the direction of arrows 64, 66 but not in the reverse direction. Valves 58, 59 are preferably made of a firm elastomeric material, such as silicone rubber, such as sold by Dow Chemical Company of Midland, Mich. as Q4765.

Support plate 50 and check valves 58, 59 are retained in position by an end cap 68 permanently mounted to housing 4, such as with an adhesive. End cap 68 has a flow path 70 which provides fluid communication between the two check valves 58, 59 and distal end 28 of accumulator chamber 10.

Body 4 also includes a guide slot 72 having a rectangular cross-sectional shape. A needle assembly 74 is mounted for slidable movement within guide slot 72 and includes a needle carrier 76 to which a hollow needle 78 is mounted. An L-shaped bore 80 is formed in needle carrier 76 to connect the proximal end 82 of needle 78 to an orifice 84 along a flat side 86 of carrier 76. Needle assembly 74 also includes protective sheath 88 which is removably mounted to the outer end 90 of needle carrier 76 so to protect against contamination of needle 78 and inadvertent injury by the needle.

Figure 1:
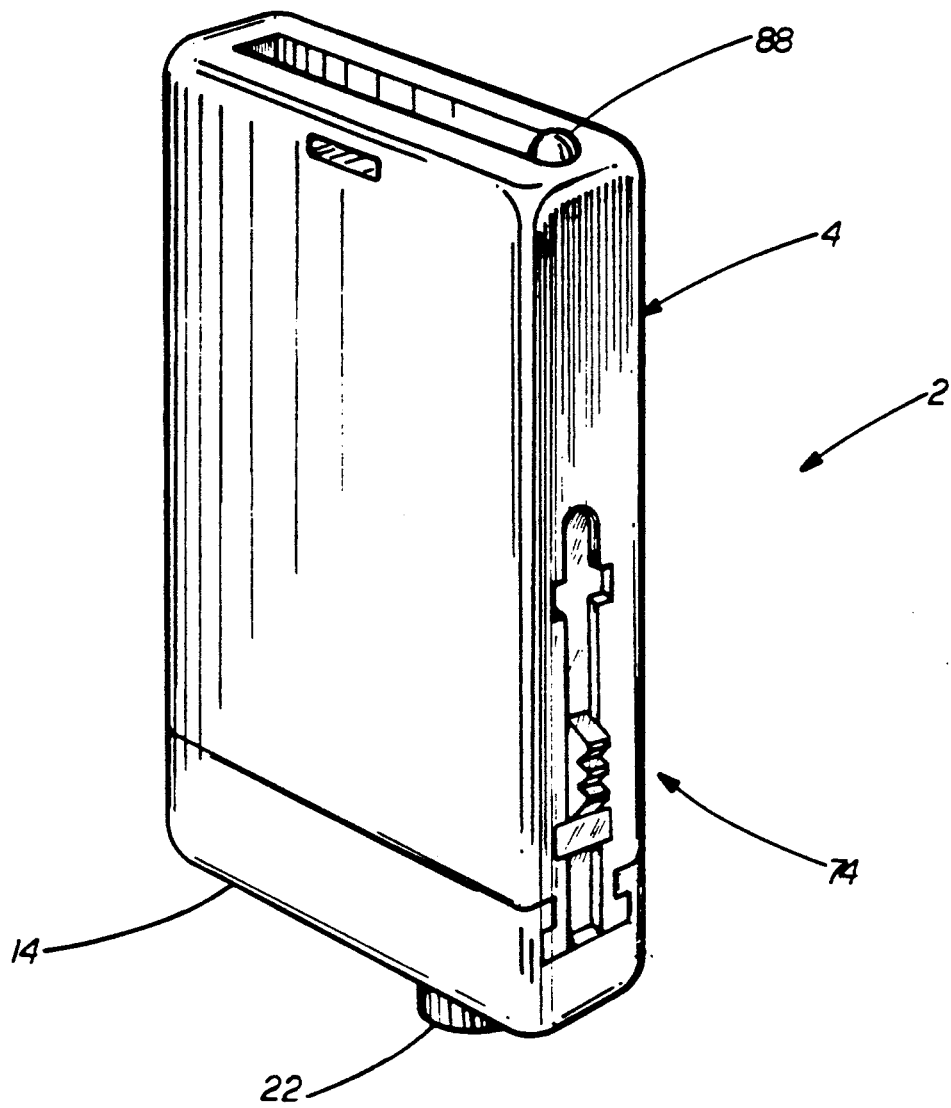
FIG. 1 is an isometric view of a syringe made according to the invention.
Figure 2:
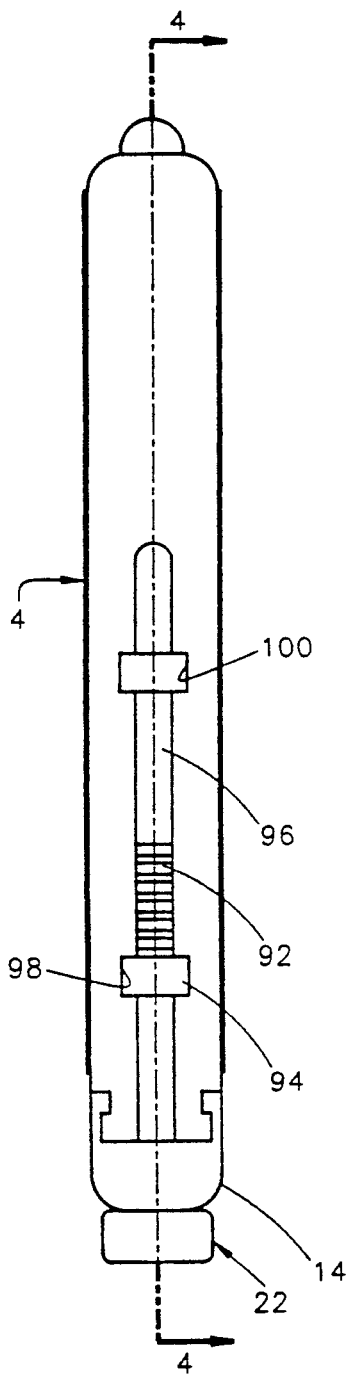
FIG. 2 is a side view thereof showing the position control button of the needle assembly.
Figure 3:
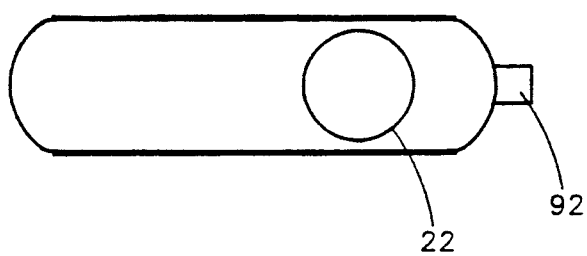
FIG. 3 is an end view thereof showing the finger engagement surface of the stem.
Figure 8:
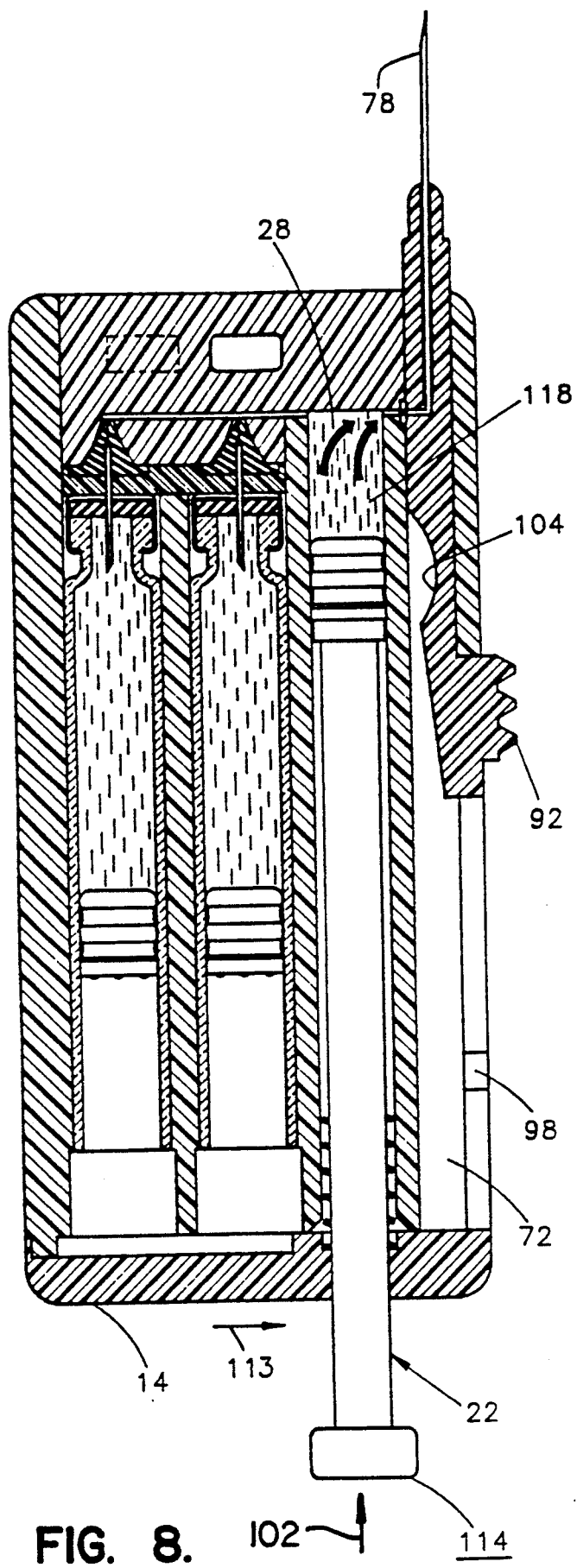
FIG. 8 shows the syringe of FIG. 6 with the end cap shifted back to the position of FIG. 4, the needle assembly in its extended position with the needle sheath removed, and the stem beginning to drive the accumulator piston to force the mixed liquid out of the accumulator chamber and through the hollow needle.
Figure 9:
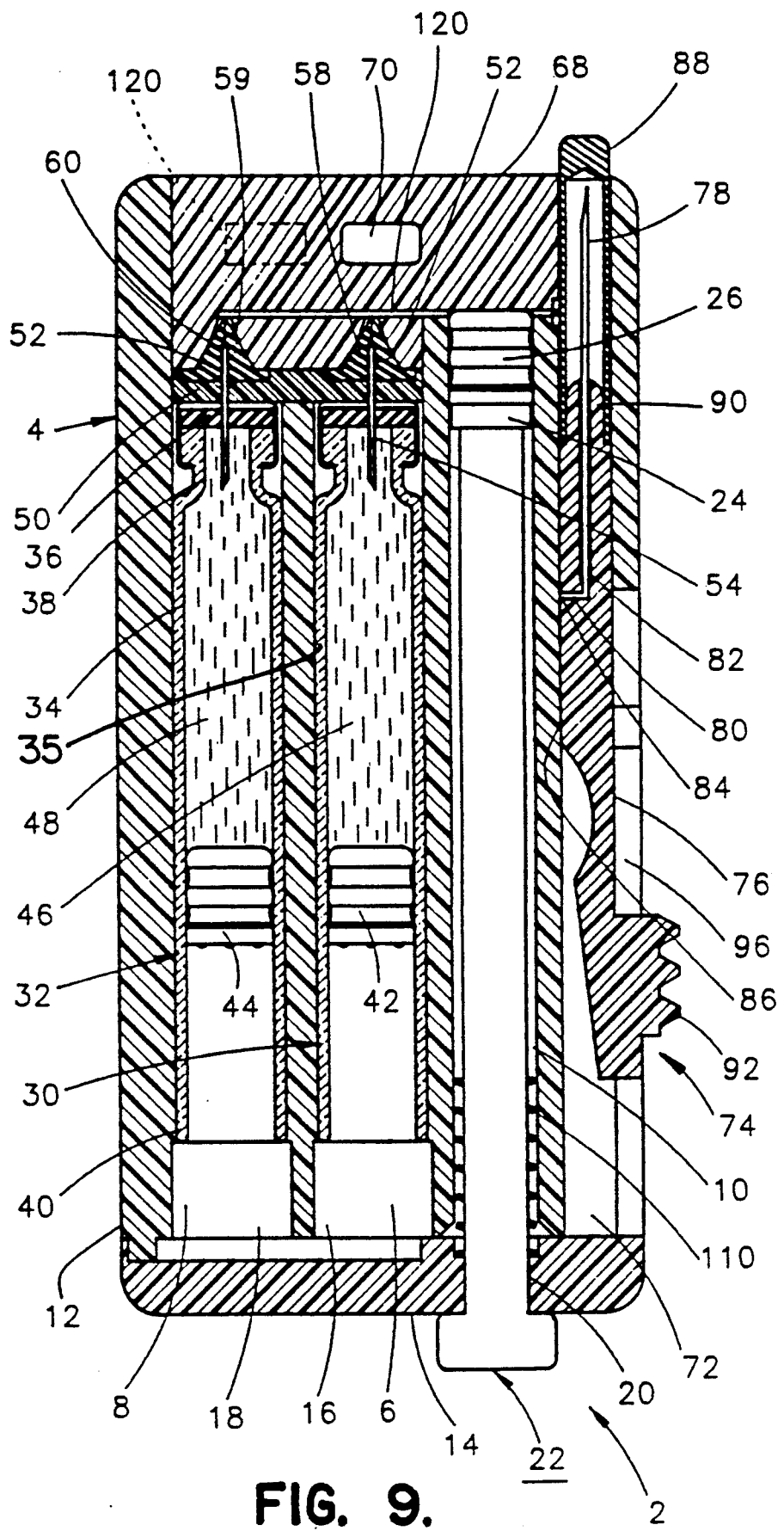
FIGS. 9 shows the syringe of FIG. 8 following an injection with the needle assembly in the retracted position.

Needle carrier 76 includes a push button 92 having an enlarged end 94, see FIG. 2. Push button 92 is sized to move along a slot 96 while enlarged end 94 is sized to engage enlarged sections 98, 100 of slot 96. To move enlarged end 94 from enlarged section 98, as shown in FIGS. 2 and 4, to enlarged section 100, shown in FIG. 8, the user presses down upon push button 92 and slides needle assembly 74 in the direction of arrow 102 as shown in FIG. 8. An appropriate resilience is provided to needle carrier 76 by a cross-sectional decrease at 104 in the needle carrier. With needle carrier 76 in the extended position of FIG. 8, orifice 84, which opens into L-shaped bore 80, is aligned with an end 106 of a bore 108 (see FIG. 7), thus fluidly coupling distal end 28 of accumulator chamber 10 to hollow needle 78.

Figure 5:
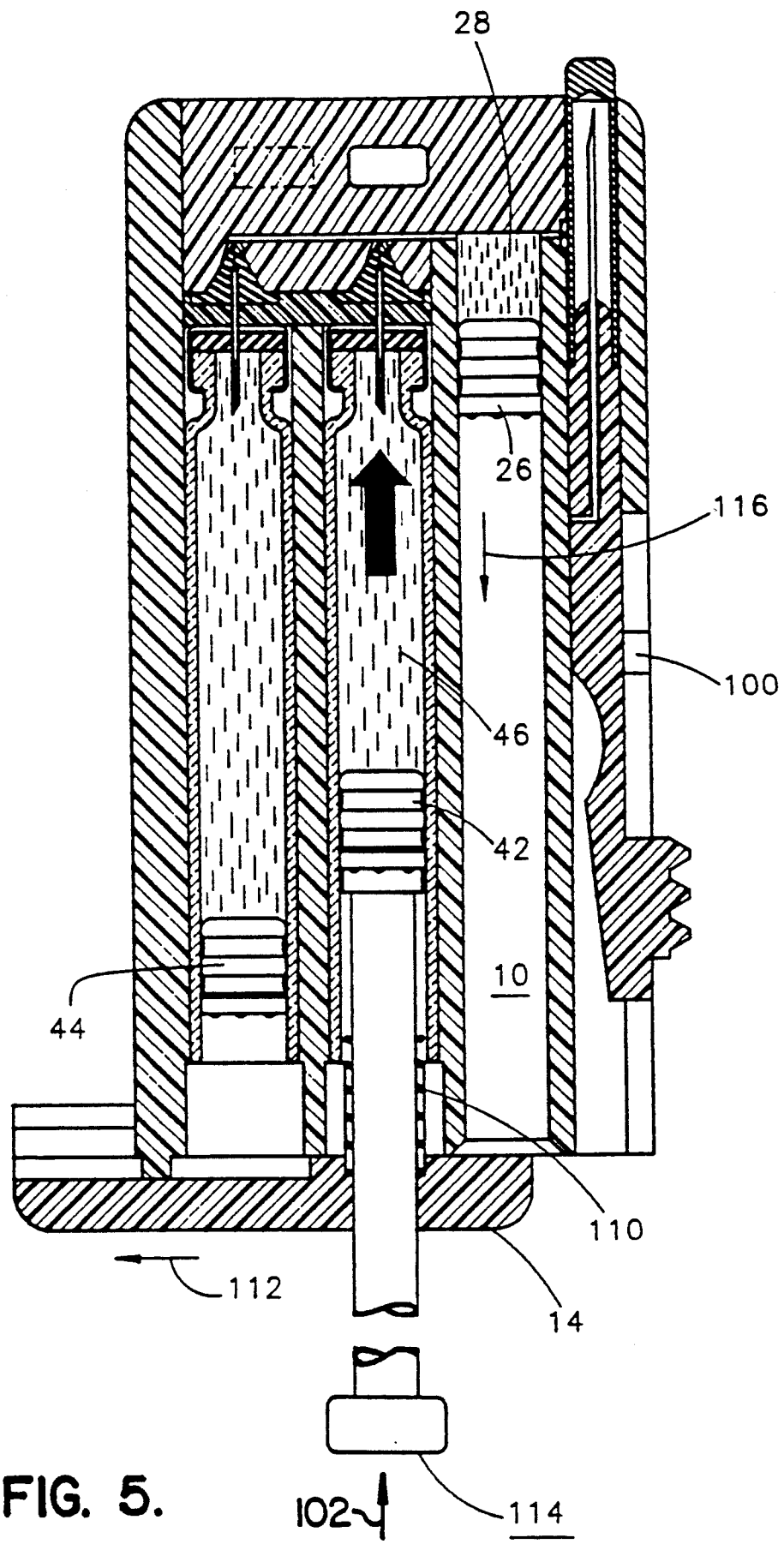
FIG. 5 is a cross-sectional view of the syringe of FIG. 4 with the end cap shifted and the plunger driving the first piston of the first cartridge forcing the first liquid into the accumulator chamber.

To move stem 22 from the position of FIG. 4 to the position of FIG. 5, the user first withdraws stem 22 as far as possible from accumulator chamber 10. During the final movement of stem 22 from chamber 10, a coil spring 110 is compressed. End cap 14 is then moved in the direction of arrow 112. After stem 22 is no longer aligned with accumulator chamber 10, the user can release stem 22. Once stem 22 becomes aligned with first chamber 6, spring 110 automatically forces stem 22 into the first chamber, thus aiding proper axial alignment. The user then presses against the outer finger engaging surface 114 of stem 22 forcing first piston 42 in the direction of arrow 102. This causes first liquid 46 to flow through spike 52, check valve 58, flow path 70, and into distal end 28 of accumulator chamber 10. The fluid pressure of liquid 46 within chamber 10 causes accumulator piston 26 to move in the direction of arrow 116. Liquid 46 is not forced into second cartridge 32 due to the use of check valve 59.

Figure 6:
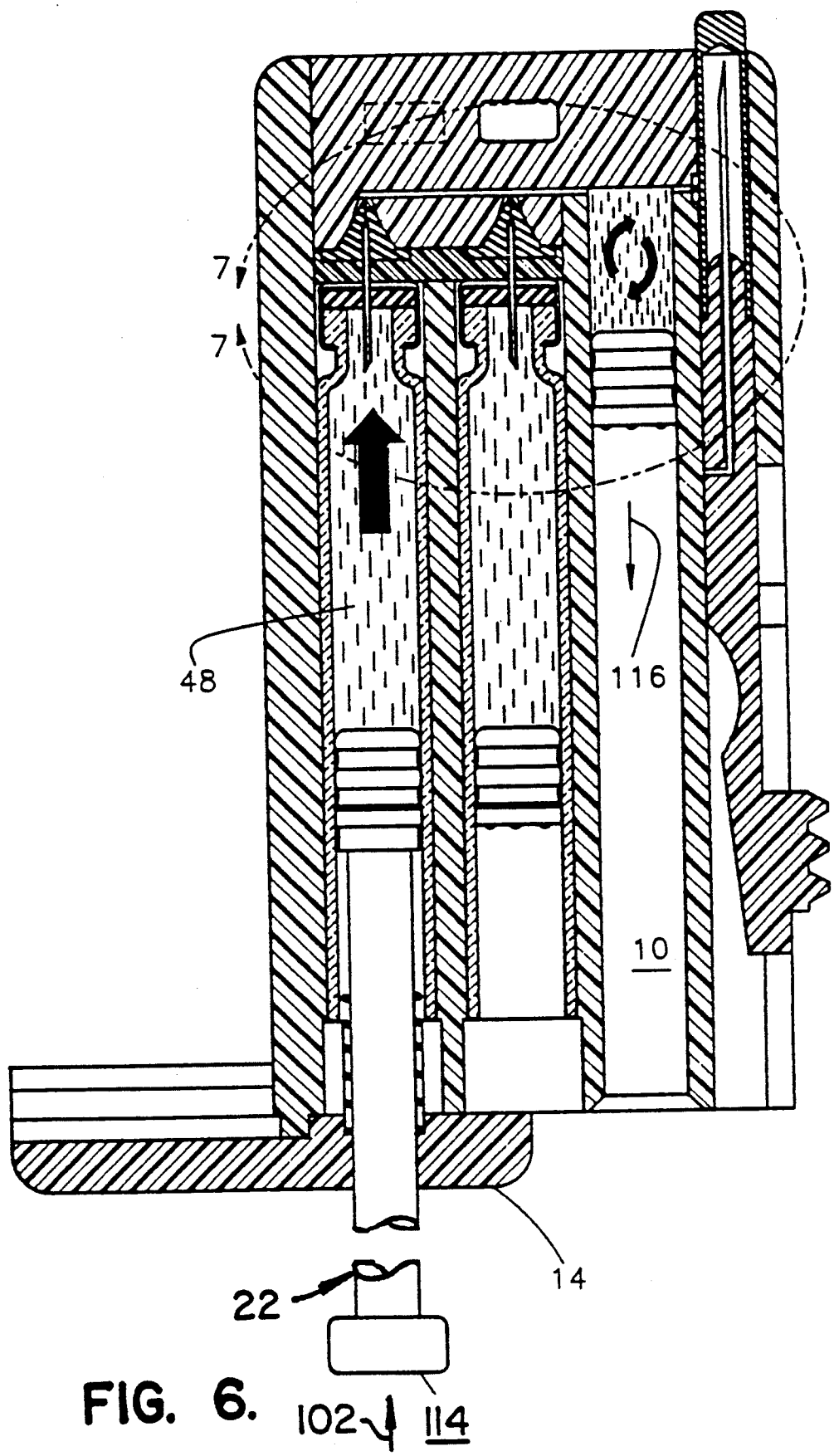
FIG. 6 shows the syringe of FIG. 5 with the end cap shifted to another position and the stem engaging the second piston of the second cartridge forcing the second liquid into the accumulator chamber where it mixes with the first liquid.

After a sufficient amount of liquid 46 has been introduced into distal end 28 of chamber 10, stem 22 is then again withdrawn and cap 14 is again slid in the direction of arrow 112 until stem 22 becomes aligned with second chamber 8. The above process is repeated for second liquid 48 as shown in FIGS. 6 and 7 to create a mixed liquid 118 in distal end 28 of accumulator chamber 10.

Stem 22 is then withdrawn from second chamber 8 and end cap 14 is moved in direction of arrow 113 to the position of FIG. 8. Push button 92 is then depressed and needle assembly 74 is driven from the position of FIG. 6 to the position of FIG. 8. Protective sheath 88 is then removed and one end of the sheath is inserted into a blind storage hole 120 formed in end cap 68. The injection is given by pressing on surface 114 of stem 22 which causes the mixed liquid 118 to flow through bore 108, bore 80 and hollow needle 78.

Figures 10A, 10B:
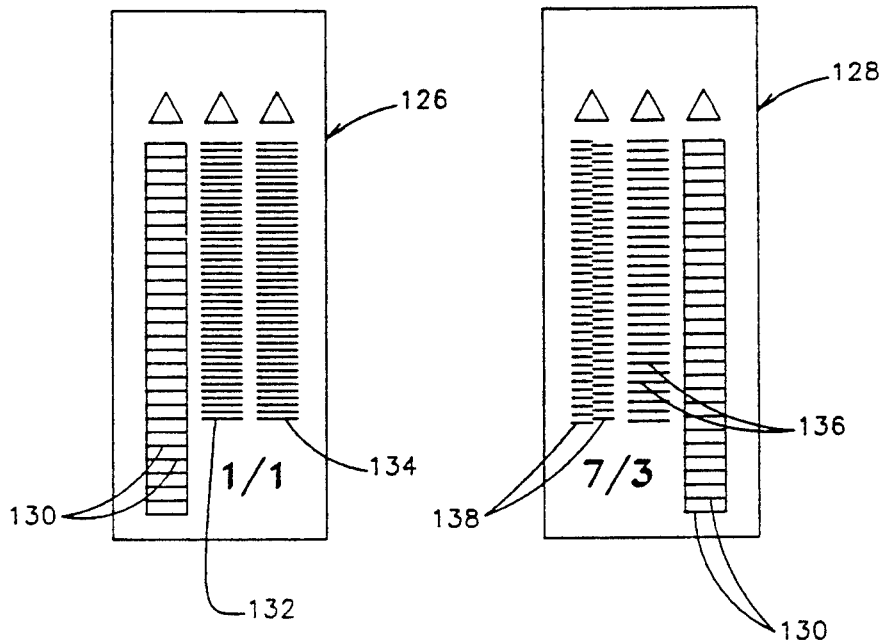
FIGS. 10A and 10B are front views of transparent dosage labels.

The amount of liquids 46, 48 forced into distal end 28 of accumulator chamber 10 can be gauged through the use of transparent dosage labels 126, 128 shown in FIGS. 10A and 10B. Label 126 includes accumulator calibrations 130. Labels 126, 128 are transparent except for the markings shown in FIGS. 10A and 10B to provide an unimpeded view of the contents of cartridges 30, 32 and accumulator chamber 10. The space between each calibration 130 equals one unit of medication. Label 126 also include first and second pharmaceutical calibrations 132, 134. Calibrations 132, 134 are each spaced apart by distances equal to one-half of a unit of medicine. Therefore, if the user moves pistons 42, 44 from one calibration 132, 134 to the next calibration 132, 134, equal amounts (one-half unit each) of liquids 46, 48 will be forced into accumulator chamber 10 to move piston 26 a distance equal to the distance between successive calibrations 130.

Label 128, mounted to the opposite side of body 4 as label 126, is used when the proportion of first liquid 46 to second liquid 48 is 7 to 3. The distance between successive first and second pharmaceutical calibrations 136, 138 corresponds to 70% of a unit and 30% of a unit respectively. Note that successive calibrations 138 are staggered—otherwise they could be too close together for easy reading. Labels 126, 128 are preferably removable so that labels having other calibrations for other mixture can be used as well.

Once the injection is complete, sheath 88 is removed from hole 120 and safely replaced over needle 78, button 92 is depressed to disengage enlarged end 94 from enlarged section 100, and needle 74 is brought back to its retracted position of FIGS. 4–6. Releasing push button 92 permits large end 94 to once again engage enlarged section 98 to keep the needle assembly from inadvertently being extended.

A fluid seal is provided at end 106 of bore 108 by an O-ring 124 as shown in FIG. 7. O-ring 124 engages the outer surface of sheath 88 when needle assembly 74 is in its retracted position of FIGS. 4–6 and presses against flat side 86 of needle carrier 76 in the region surrounding position 84 and the end of L-shaped bore 80 when in the extended position of FIG. 8. Instead of using a separate O-ring, other types of seals, including a molded-in, outwardly extending ring seal, could be used. Also, to aid sterility, a check valve can be used adjacent O-ring 124; this can be especially useful when a removable needle assembly is used.

The advantage of using blind hole 120 to temporarily house sheath 88 causes the sheath to extend laterally outwardly from the syringe during use. Thus, if the user inadvertently forgets to replace the sheath before withdrawing needle assembly back into guide slot 72, sheath 88 will immediately get in the way when the user attempts to store the syringe in the user's pocket, purse or carrying pouch. Also, if safety sheath 88 is not in place when pistons 42, 44 are depressed, liquid may leak through bore 108 and out guide slot 72. Thus, the user has an additional reason for properly maintaining safety sheath 88 in place.

For the convenience of the user, a through hole 122 can be provided through end cap 68 to permit syringe 2 to be carried, for example, on a keychain.

Figures 11A, 11B:
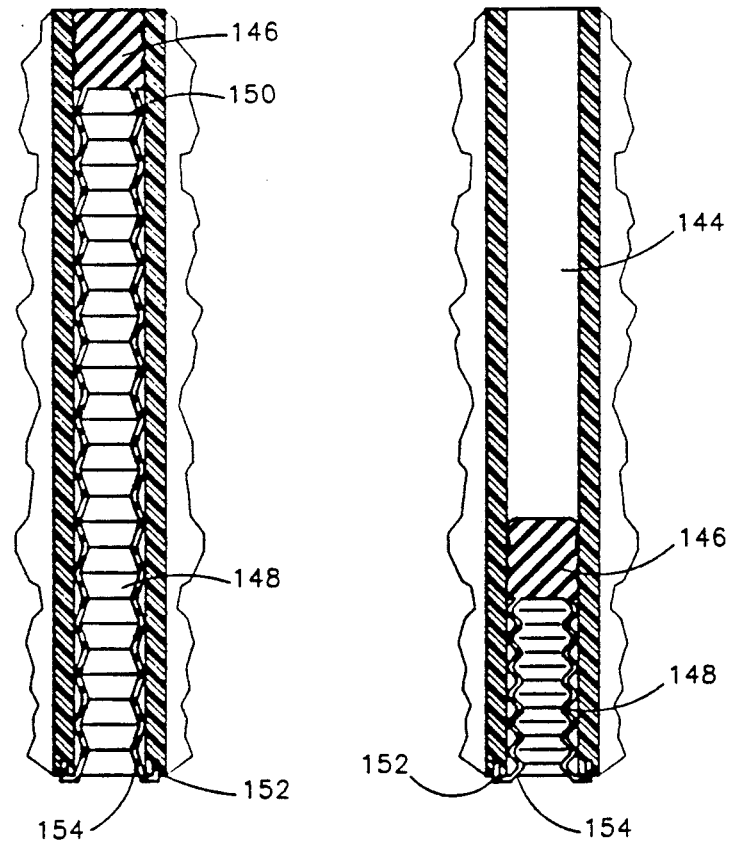
FIGS. 11A and 11B are simplified views showing the accumulator piston and chamber of FIGS. 4 and 5 used with a sterility skirt.

FIGS. 11A and 11B illustrate, in schematic form, an accumulator chamber 144 housing an accumulator piston 146 and a sterility skirt 148. Skirt 148 is a lightweight, fluid impervious, flexible tubular material, such as silicone rubber, secured to piston 146 at one end 150 of skirt 148 and to the proximal end 152 of chamber 144 at the other end 154 of skirt 148. Skirt 148 is in its extended condition of FIG. 11A when piston 146 is fully within chamber 144 and in its compressed condition of FIG. 11B when piston 146 is near proximal end 152. Therefore, skirt 148 and piston 146 to help keep the inner walls of chamber 144 sterile during use and between uses. Other methods for insuring sterility is maintained can be used as well.

FIGS. 12–16 illustrate a further embodiment of the invention. Syringe 160 includes a body 162 defining first, second and third chambers 164, 166, 168. Chambers 164, 166 are separated into distal ends 170, 172 and proximal ends 174, 176 by annular shoulders 178, 180. Distal ends 170, 172 are sized for receipt of first and second pharmaceutical cartridges 182, 184, cartridge 182 having a larger diameter and a larger volume than cartridge 184, typically 3 ml versus 1½ ml. Cartridges 182, 184 are secured to a manifold base and accumulator chamber assembly 186. See FIG. 17. Assembly 186 includes sharpened hollow spikes 188 used to pierce the septums 190 of cartridges 182, 184. Cartridges 182, 184 are secured to assembly 186 through the engagement of projections 192 extending inwardly from clips 194, four of which surround each spike 188, with a proximally facing edge 196 of a collar 198. Assembly 186 also includes a portion 200 defining an accumulator chamber 202, portion 200 fitting within third chamber 168 of body 162.

Assembly 186 includes a cylindrical extension 204 which fits snugly within a complementarily shaped blind bore 206 formed within an elastomeric manifold check valve 208. See FIGS. 18–21. Check valve 208 is preferably of a 50 durometer rubber, such as silicone rubber, and includes a pair of extensions 210 each having a cylindrical outer surface and a conical inner surface 212. Extensions 210 are sized for complementary mating engagement within tapered openings 214 formed within assembly 186. See FIGS. 16 and 22. When assembly 186 and manifold check valve 208 are assembled, extensions 210 engage tapered openings 214 to act as check valves while cylindrical extension 204 fits snugly within blind bore 206.

Figure 22:
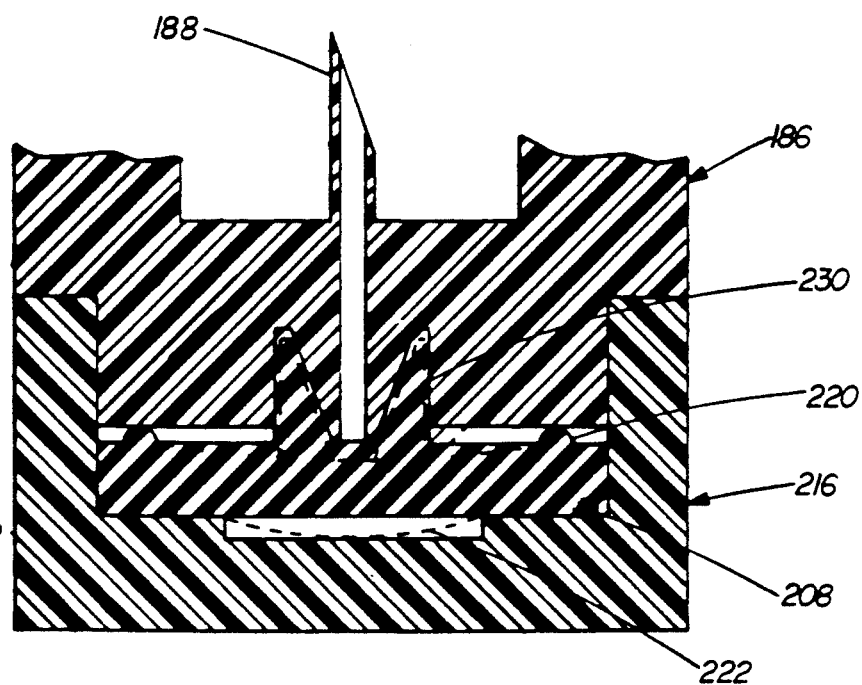
FIG. 22 is an enlarged cross-sectional view showing the replaceable fluid path cartridge of FIG. 12 and illustrating, in exaggerated form, the movement of the manifold check valve from its solid line position of FIGS. 12 and 12A to a dashed line position, thus opening up a fluid pathway between the interior of the associated cartridge and the accumulator chamber.
Figure 18:
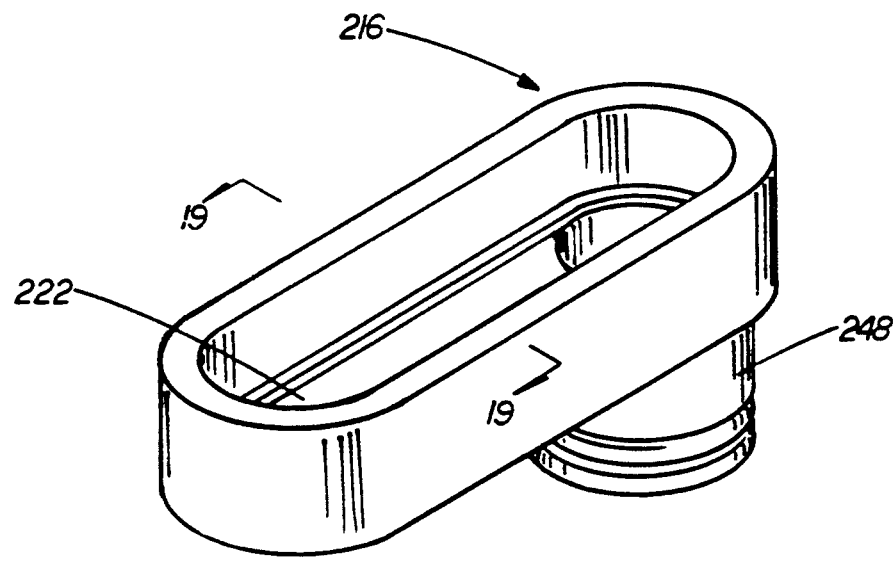
FIG. 18 is an isometric view of the manifold cover of FIG. 16.
Figure 19:
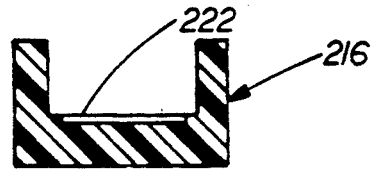
FIG. 19 is a cross-sectional view taken along line 19—19 of FIG. 18 with the depth of the channel exaggerated for purposes of illustration.
Figure 20:
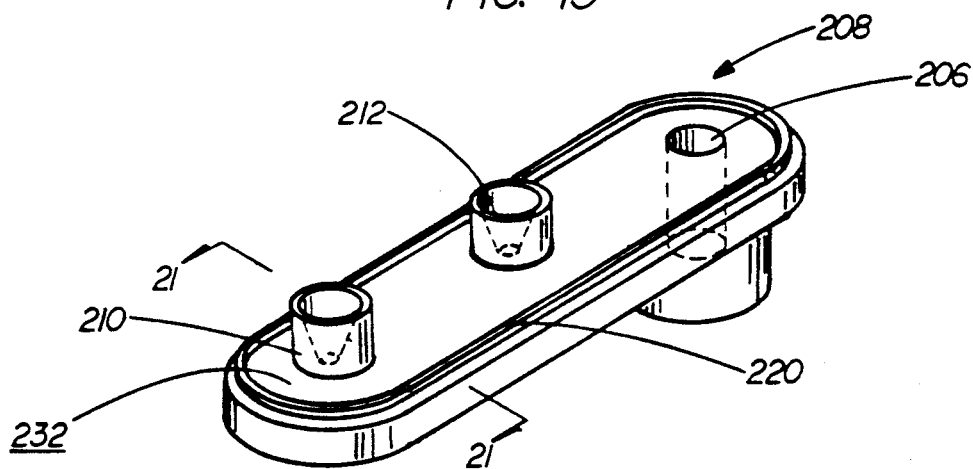
FIG. 20 is an isometric view of the manifold check valve of FIG. 16.
Figure 21:
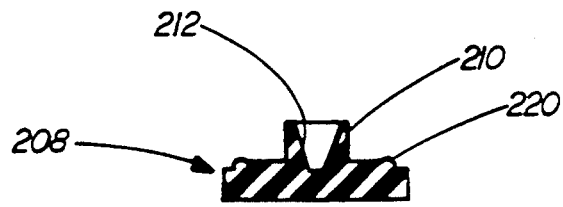
FIG. 21 is a cross-sectional view taken along line 21—21 of FIG. 20.

A manifold cover 216 is secured to assembly 186 along their intersecting surfaces 218, see FIG. 22, using an adhesive or ultrasonic welding techniques. Doing so securely captures manifold check valve 208 between assembly 186 and manifold cover 216 so that a perimeter ring seal 220 formed on manifold check valve 208 provides a tight seal against assembly 186. Cover 216 includes a channel 222, typically 3.2 mm. wide and 0.38 mm. deep. Channel 222 permits manifold check valve 208 to deflect into the channel, as shown in dashed lines in FIG. 22, when one of the pistons 224, 225 of cartridges 182, 184 are driven along the length of the cartridges to force one of the liquid pharmaceuticals 226, 228 past the structures 210, 214 which form a check valve 230. The liquid pharmaceutical then flows between a surface 232 of manifold check valve 208 and a surface 234 of assembly 186, between cylindrical extension 204 and blind bore 206, through the bore 236 formed in extension 204, see FIG. 12A and into accumulator chamber 202. This causes accumulator piston 238 to move in the proximal direction, that is, in the direction of arrow 240. Piston 238 has an integrally formed sterility skirt 242 having a folded back portion 244 which is secured against the surface portion 200 of assembly 186 by a sealing ring 246.

Figure 16:
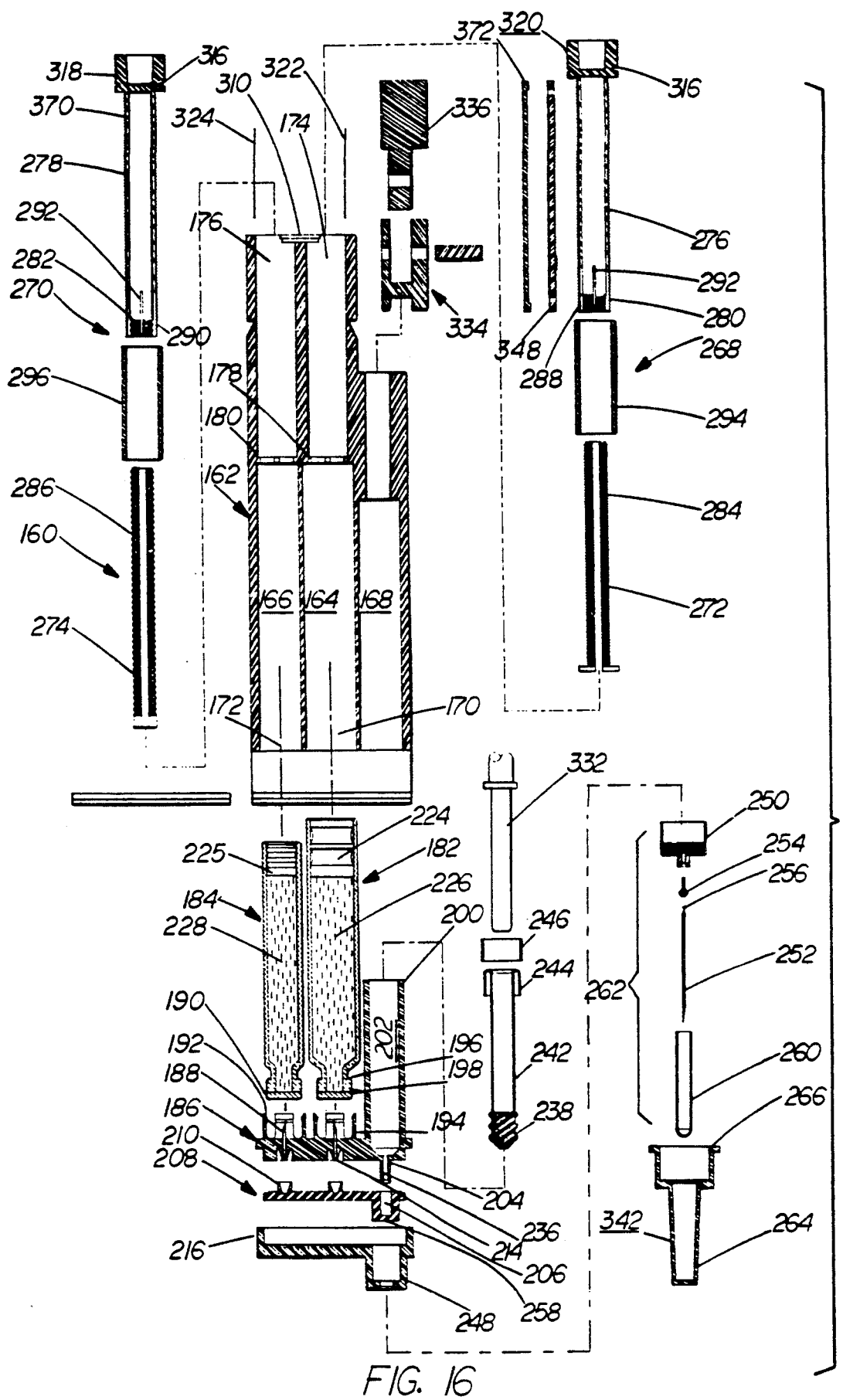
FIG. 16 is an exploded cross-sectional view of the syringe of FIG. 12.
Figure 17:
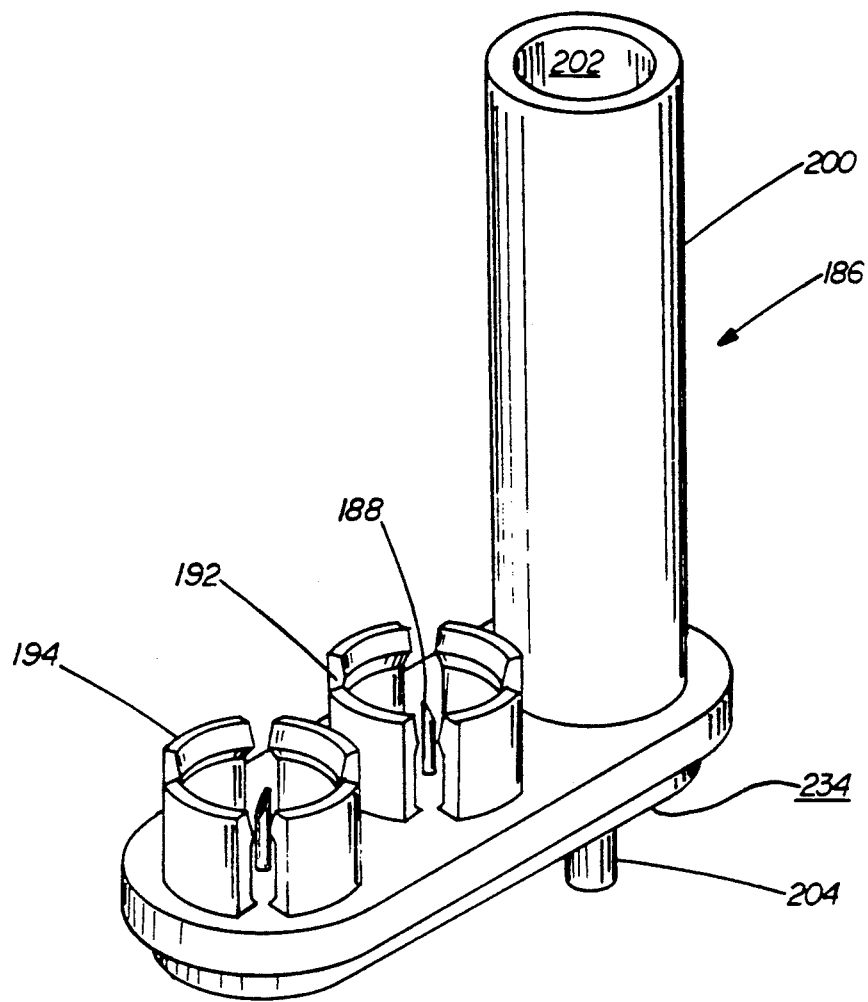
FIG. 17 is an isometric view of the manifold base and accumulator chamber assembly of FIG. 16.

Manifold cover 216 has a threaded boss 248 to which an internally threaded needle hub 250, see FIG. 16, can be mounted. A hollow needle canula 252 is secured to needle hub 250 by a suitable epoxy 254. Needle hub 250, hollow needle 252, inner sheath 260 and epoxy 254 constitute a needle assembly 262 such as one sold by the Becton Dickenson Company of Rutherford, N.J., which is packaged in an outer sheath 264. Needle assembly 262 is sealed within outer sheath 264 by a removable film strip, not shown, secured to an edge 266 of sheath 264.

Needle 252 has a sharpened inner end 256 which pierces that portion 258 of manifold check valve 208 covering the end of blind bore 206 when needle assembly 262 is mounted to 248. This occurs after the desired mixture of pharmaceuticals 226, 228 has been accumulated in chamber 202. Needle 252 is generally covered by a sheath 260 for safety and sanitary purposes. Needle assembly 262 and sheath 264 are typically disposed of after each use. Outer sheath 264 not only protects needle assembly 262 against damage and contamination, but sheath 264 is also used while metering liquid pharmaceuticals 226, 228 from cartridges 182, 184 and into accumulator chamber 202 as will be discussed in detail below.

Pistons 224, 225 are driven by stem assemblies 268, 270 which are housed within proximal ends 174, 176 of chambers 164, 166. Stem assemblies 268, 270 include externally threaded stems 272, 274 sized to fit within hollow stem drivers 276, 278. Stem drivers 276, 278 have internal threads 280, 282 which engage the external threads 284, 286 formed along substantially the entire lengths of stems 272, 274. The distal ends 288, 290 of stem drivers 276, 278 have four slits 292 formed therein. Slits 292 permit distal ends 288, 290 to separate to permit stems 272, 274 to move axially within stem drivers 276, 278 by permitting the threads to override one another. Stem assemblies 268, 270 also include locking collars 294, 296 sized to fit over the outside of stem drivers 276, 278. As shown in FIGS. 13B and 13C, locking collars are axially positioned using a button 298 mounted within a cutout 300 formed in body 162. A pair of pins 302 extend from button 298, pass through slots 304, 306 to engage locking collars 294, 296. By manipulation of axially movable button 298, locking collars 294, 296 can be moved from the locked position of FIG. 12 overlying distal ends 288, 290 of stem drivers 276, 278 to an unlocked position by moving button upwardly relative to FIGS. 12 and 13B. This permits distal ends 288, 290 to expand when stems 272, 274 are pulled from or pushed into stem drivers 276, 278 allowing the user to reset the stems.

Figure 28:
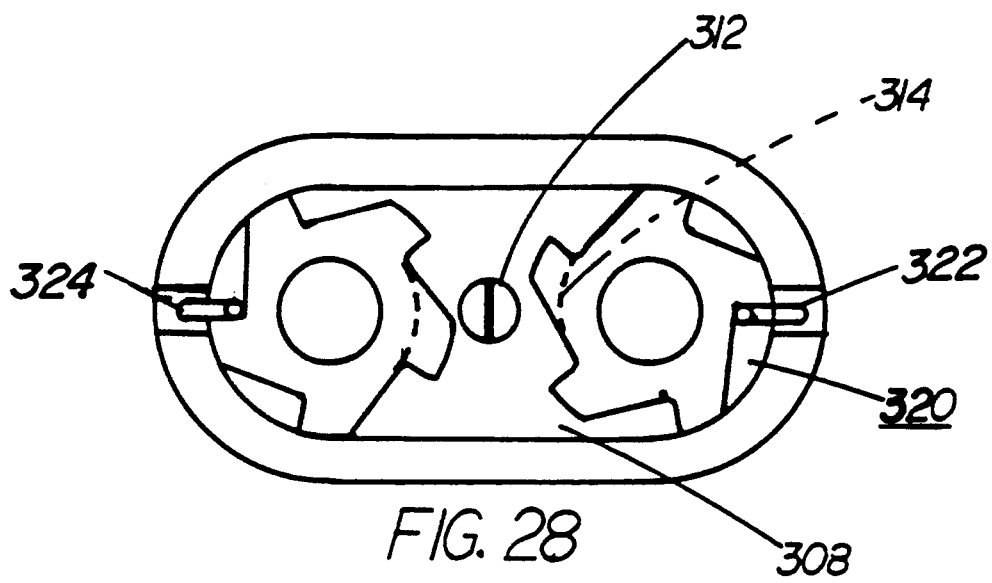
FIGS. 26–28 are simplified front, side and end views illustrating the detent mechanisms used with the stem drivers of FIG. 16.
Figure 26:
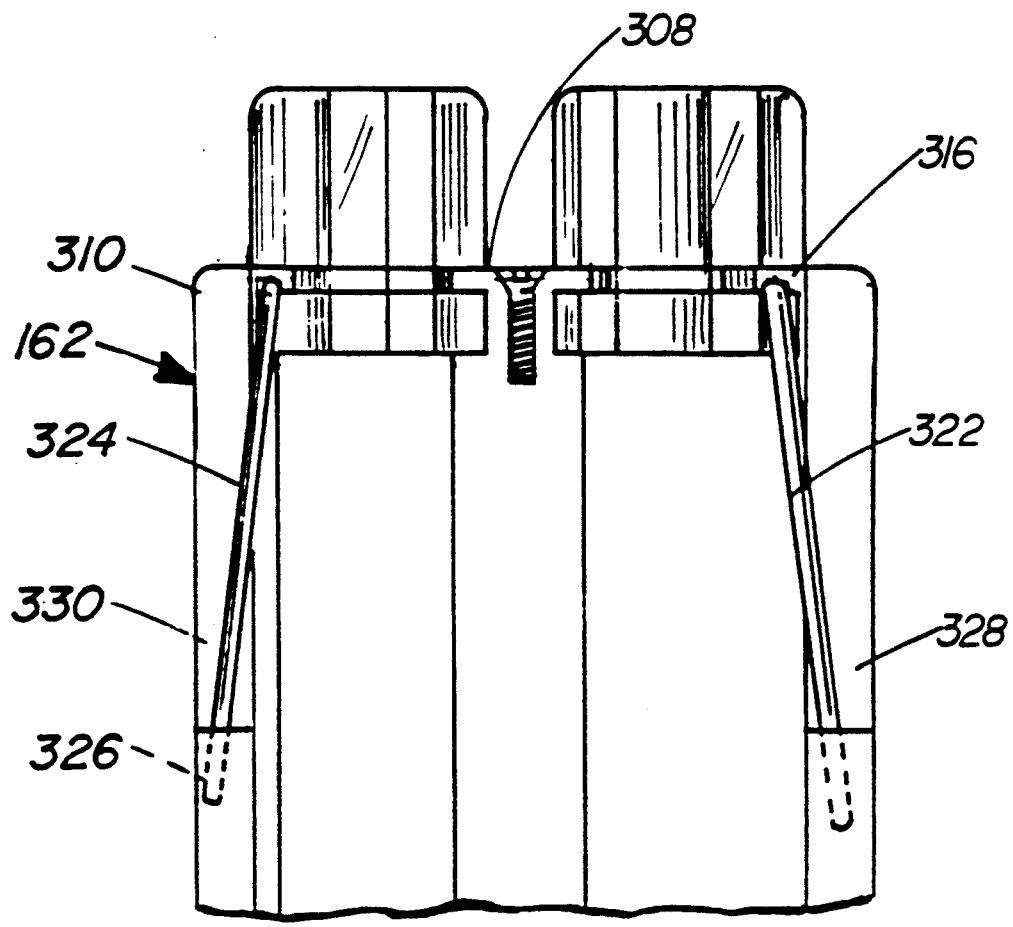
Figure 27:
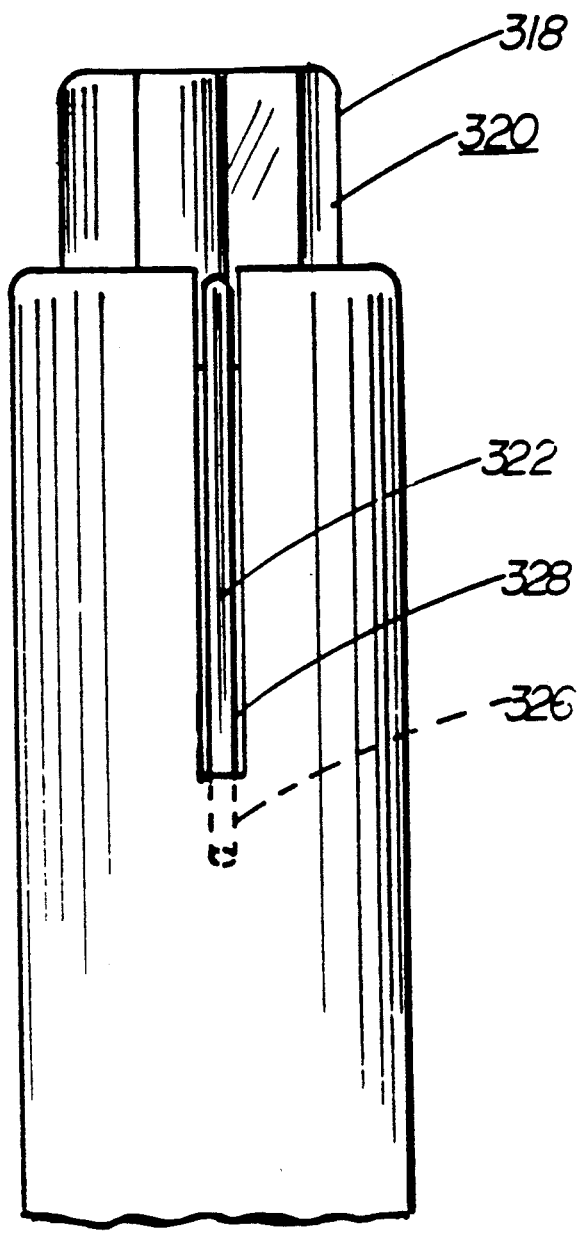

Stem drivers 276, 278 are free to rotate within proximal ends 174, 176 but are retained therein by a yoke 308, see FIGS. 26–28, which is secured to the proximal end 310 of body 162 by a screw 312. Yoke 308 has a pair of arcuate cutouts 314 which fit within annular slots 316 formed in the proximal ends 318 of stem drivers 276, 278. Proximal ends 318 include a ratcheted outer surface 320. Spring wires 322, 324 are mounted within holes 326 at the end of slots 328, 330. Holes 328, 330 are formed at an angle so that spring wires 322, 324 press against ratcheted outer surfaces 320 of stem drivers 276, 278.

As the user rotates stem drivers 276, 278, the stem drivers remain axially in place but cause stems 274, 276 to press against pistons 224, 225 respectively. Doing so causes the pharmaceuticals 226, 228 to enter accumulator chamber 202 and drive accumulator piston 238 upwardly in FIG. 12. Needle assembly 262 is then mounted to threaded boss 248 so that sharpened inner end 256 pierces portion 258 of manifold check valve 208. The movement of piston 238 upwardly in FIG. 12, that is in the proximal direction, causes an accumulator stem 332 to move upwardly in FIG. 12. This causes a thumb driver assembly 334 mounted to the proximal end 335 of accumulator stem 332 to also move upwardly in FIG. 12. To make the injection, pivotal thumb support 336 of thumb driver assembly 334 is pivoted in the direction of arrow 338 of FIG. 13. Sheath 260 is then removed and the injection is given by pressing on thumb support 336.

Figure 12:
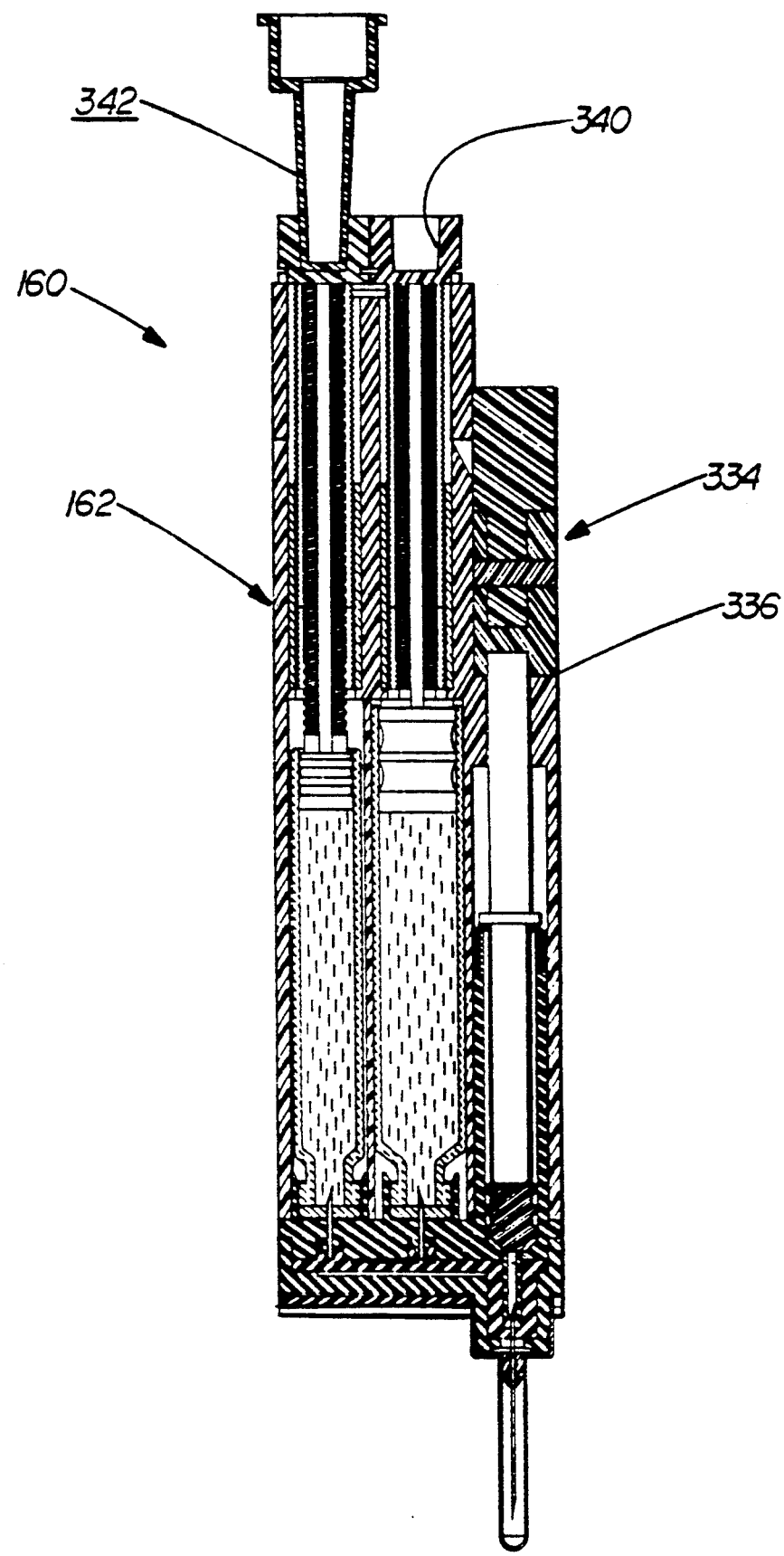
FIG. 12 is a cross-sectional view of an alternative embodiment of the syringe of FIG. 4 shown in the pre-use condition.

As suggested in FIG. 12, outer sheath 264 can be used to provide the user with an additional mechanical advantage in the rotation of stem drivers 276, 278. Proximal ends 318 have tapered openings 340 sized to frictionally engage the tapered outer surface of outer sheath 264.

Referring now to FIGS. 13A, 23, 24 and 25, syringe 160 is seen to include an optical dose indicator 346 pivotally mounted to body 162. Indicator 346 includes a frame 348 having a pair of cutouts 350. Within each cutout 350 is a support surface 352 and a guide slot 354 defined within a guide slot extension 356. A continuous loop indicator ribbon 358 having a line of demarcation 360 is positioned over and around each support surface 352. A follower 362 having a pair of slots 364 on its upper end is mounted within slot 354 for movement along slot 354. Follower 362 includes a ribbon gripper 366 which securely grips ribbon 358 using an adhesive along the lower reach of the ribbon.

Figure 13:
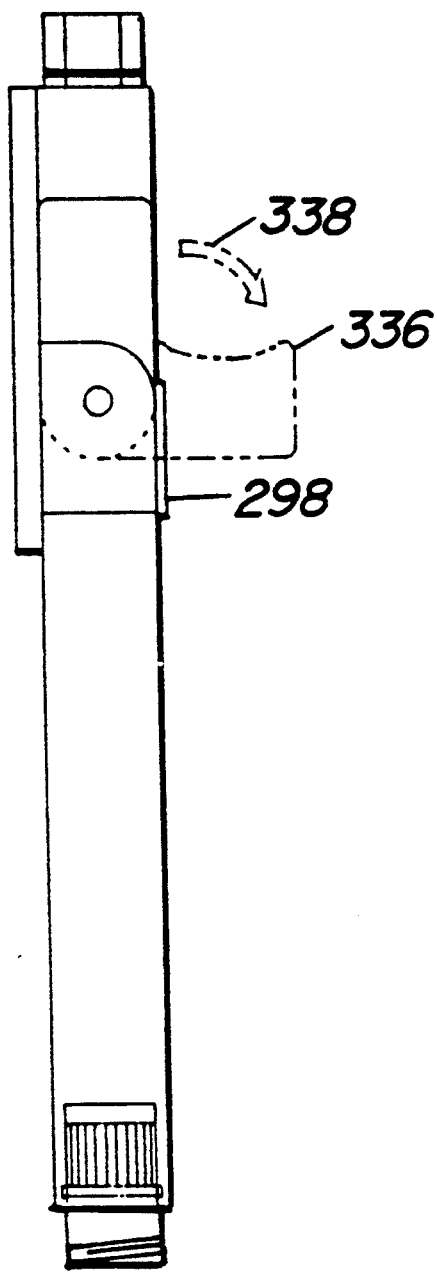
Figure 13A:
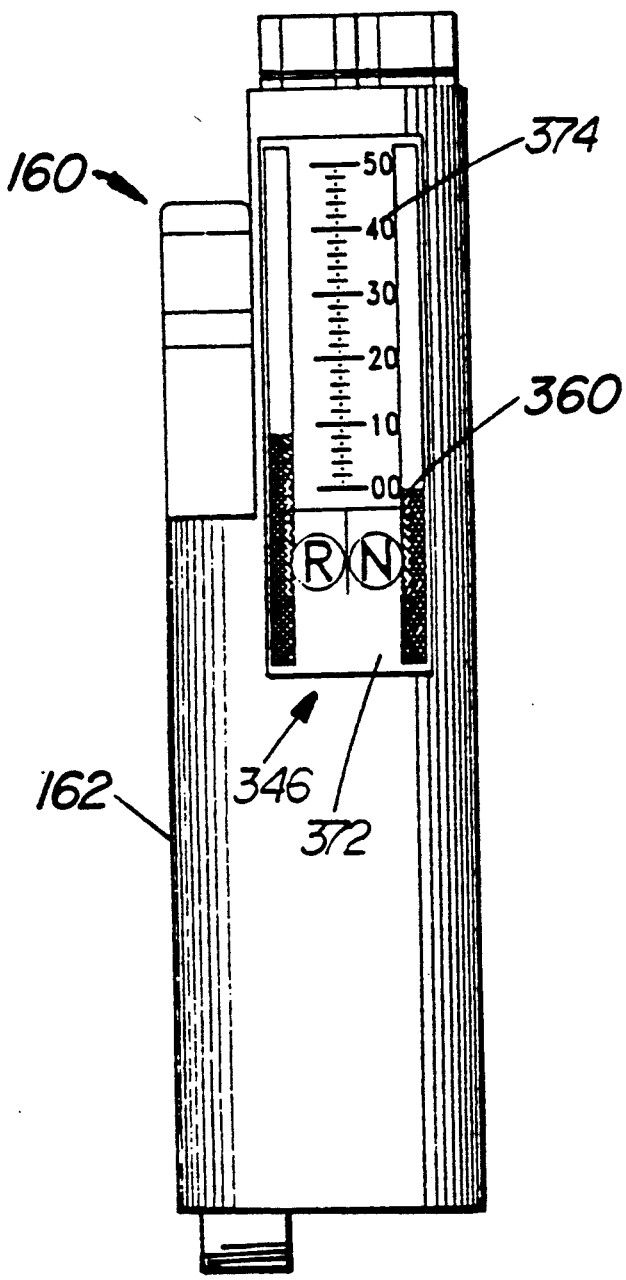

Follower 362 has teeth 368 sized to engage teeth 370 formed on the outer surface of stem drivers 276, 278. FIG. 16 illustrates frame 348 with a clear cover 372 positioned above the frame. Cover 372, as shown in FIG. 13A, has numerical indicia 374 on cover 372. This permits the user to clearly determine the size of the dose, typically in units of medicine, by the location of line of demarcation 360 relative to indicia 374. It is preferred that follower 362, and thus line of demarcation 360, move at a greater linear speed than the corresponding piston 224, 225. In preferred embodiment, this is a 2 to 1 ratio so that if external threads 284 are spaced at 20 threads per inch, teeth 368, 370 are spaced at 10 threads per inch for a 2 times amplification. Since the distances moved are generally relatively small, this can greatly help the user determine the dose for each component, especially those users who are visually impaired.

FIGS. 29-36C disclose a further embodiment of the invention in which a multiple pharmaceutical dispenser with accumulator is illustrated in the form of a syringe 402. Syringe 402 includes a body 404 made up, in this embodiment, of four primary housing components, specifically a manifold housing 406 at the distal end of body 404, an intermediate housing 408 coupled to manifold 406 by dovetail joints 410, 412, a drive housing 414 coupled to intermediate housing 408 through dovetail joints 416, 418 and a dose knob housing 420 attached to the proximal end 422 of drive housing 414 using an appropriate adhesive. Other constructions for body 404 consistent with assembly costs and other requirements could be used as well.

Figure 12A:
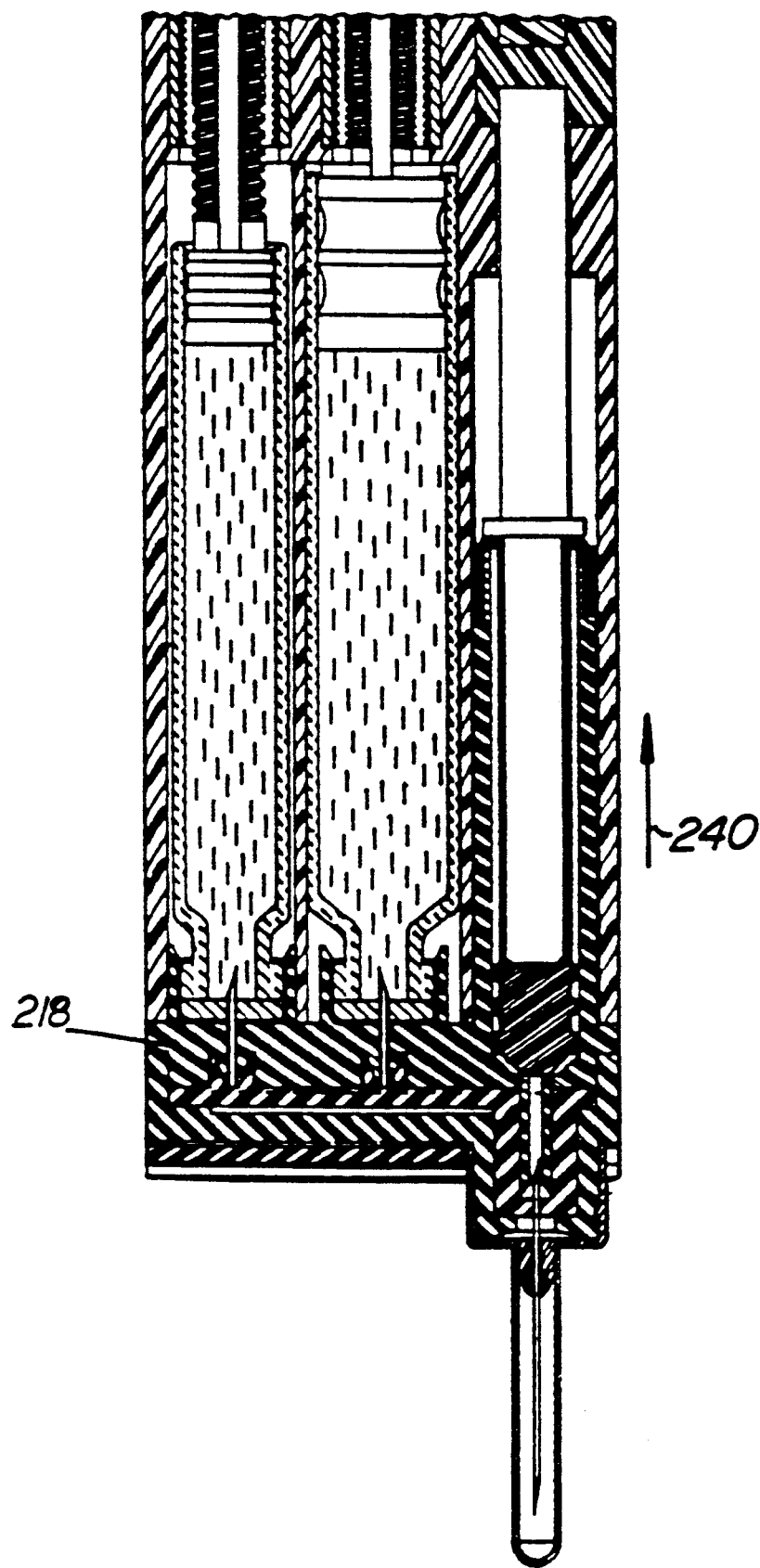
FIG. 12A is an enlarged view of the outer or distal end of the syringe of FIG. 12.
Figure 12B:
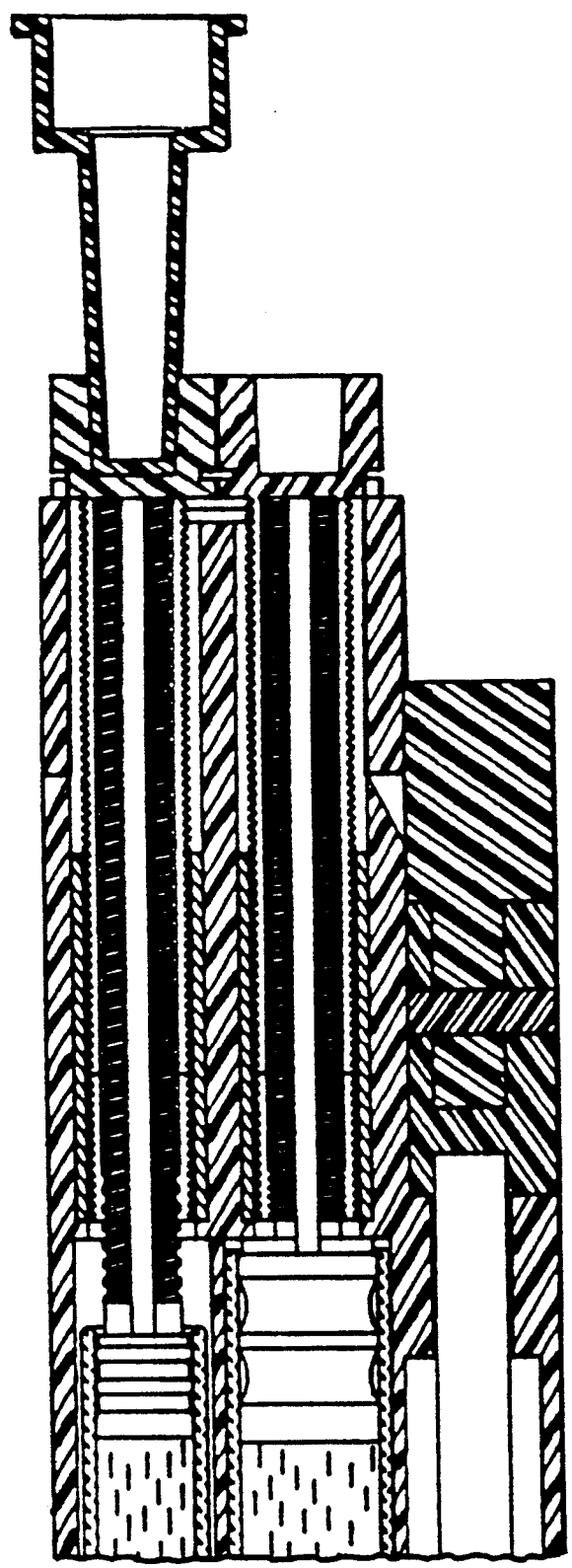
FIG. 12B is an enlarged view of the near or proximal end of the syringe of FIG. 12.

Syringe 402 also includes a manifold/cartridge/ accumulator assembly 424, which is quite similar to the corresponding components of syringe 160 shown in FIGS. 12A and 16. Assembly 424 includes a manifold cover 426 to which a needle mount assembly 428 is pivotally secured. Manifold cover 426 includes a needle mount boss 430 having a pair of intersecting slots 432, 434 configured to mount a needle mount pivot 436 to manifold cover 426. Pivot 436 has a pivot body 438 with a bore 440 formed therethrough. Body 438 has a pair of pivot pins 442 extending therefrom positioned within slots 434 to permit pivot 436 to move from the storage or retracted position of FIG. 31 90° in a counterclockwise direction to the use position of FIG. 29. Pivot mount assembly 428 also includes a septum 444 secured to pivot 436 by a septum cap 446. Pivot 436 also includes a T-shaped extension 448 which is slidably mounted to a plate 450 which covers pivot 436, and any needle assembly 451 mounted thereto, in the storage condition of FIG. 31.

Manifold cover 426 is a component of a manifold 452. Manifold 452 includes manifold cover 426, an elastomeric manifold check valve 454 and a manifold base 456 from which an accumulator barrel 458 extends. The components of manifold 452, that is manifold cover 426, check valve 454 and manifold base 456, are similar in construction to the corresponding components shown in FIGS. 17-22 and thus will not be described except where the components differ.

Manifold/cartridge/accumulator assembly 424 also includes an accumulator assembly 460 including, in addition to accumulator barrel 458, a sterile piston assembly 462 including an accumulator piston 464 from which a sterility skirt 466 extends. Sterility skirt 466 includes a rolled over portion 468 which is sized to fit over the opened proximal end 470 of accumulator barrel 458. A retaining band 472 is used to secure piston assembly 462 to accumulator barrel 458 by being placed over portion 468 of skirt 466 and open proximal end 470 of barrel 458. This construction is similar to the corresponding structure shown in the embodiment illustrated in FIG. 16. Accumulator assembly 460 also includes an accumulator stem sheath 474 which, as shown in FIG. 31, has a specially adapted tip 476 sized and shaped to engage accumulator piston 464.

Figure 31:
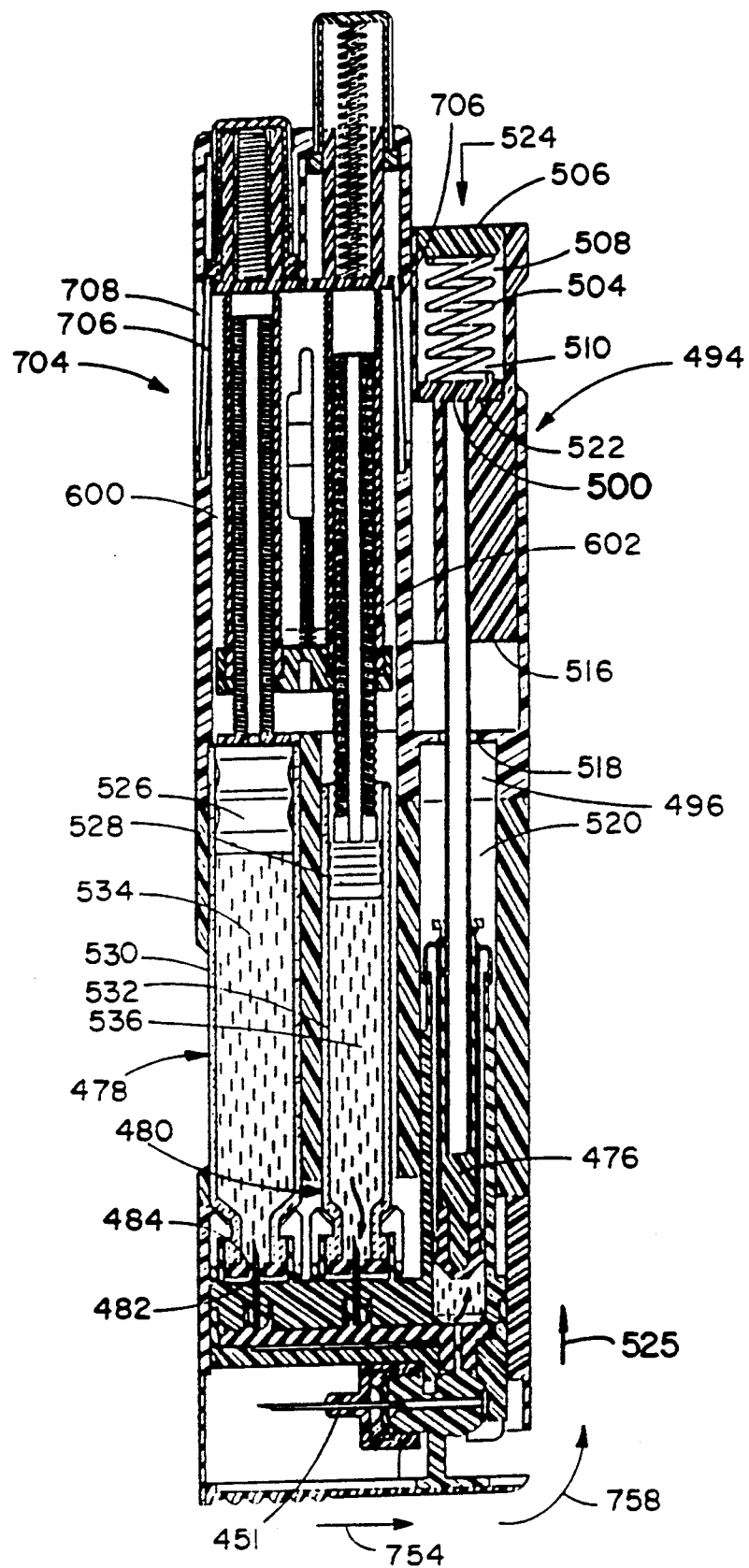
FIG. 31 is a cross-sectional view of the syringe of FIG. 29 with the needle assembly omitted and the needle mount assembly in the retracted or storage position after an amount of pharmaceutical 536 has been driven from cartridge 480 into accumulator chamber 659.

Manifold/cartridge/accumulator assembly 424 also includes a 3ml pharmaceutical cartridge 478 and a 1.5ml cartridge 480 mounted to manifold base 456 so that spikes 482, shown in FIG. 31, pierce septums 484 at the distal ends of cartridges 478, 480 as in the prior embodiment. Manifold base 456 includes a pair of positioning rings 486 extending from the manifold base surrounding spikes 482. Rings 486 guide the distal or septum ends 488 of cartridges 478, 480 onto spikes 482.

Assembly 424 also includes a pair of segmented adapter collars 490, 492 which are mounted to cartridges 478, 480 at septum ends 488. Adapter collars 490, 492 are sized so that positioning rings 486 fit between septum ends 488 and collars 490, 492, as shown in FIG. 31. Collars 490, 492 are used to insure that both of cartridges 478, 480 are properly mounted to manifold base 456 prior to inserting manifold/ cartridge/accumulator assembly 424 to body 404 as is described in more detail below.

Syringe 402 includes an accumulator stem assembly 494 housed within an accumulator bore 496 formed in drive housing 414. Accumulator stem assembly 494 includes an accumulator stem 498 having a plate 500 secured to a proximal end 502 of stem 498. Accumulator stem assembly 494 also includes an accumulator spring 504 between plate 500 and a proximal plate 506. Plates 500, 506 and spring 504 are housed within an enlarged proximal region 508 of a guide bore 510 formed within an accumulator guide sleeve 512. Guide bore 510 is sized to house the main portion 514 of accumulator stem 498. Main portion 514 is sized to extend beyond the distal end 516 of sleeve 512 and pass through a narrow opening 518, shown in FIG. 31, of accumulator bore 496, through a second accumulator bore 520 formed in housing 408 and into the interior of accumulator stem sheath 474. Proximal plate 506 is fixed in position within region 508 of guide bore 510. Plate 500 is biased against a shoulder 522, defining the proximal end of region 508, by spring 504.

FIG. 31 illustrates accumulator stem assembly 494 in a pre-use condition and as assembly 494 would be at the end of a delivery stroke. The use of plates 500, 506 and spring 504 permit the user to continue pressing on stem assembly 494 in a distal direction 524. Doing so permits plate 506 and guide sleeve 512 to move in distal direction 524 as suggested by the dashed lined position of assembly 494 in FIG. 29. This extra motion of accumulator stem assembly 494 causes spring 504 to compress; however, accumulator stem 498 is at the limit of its distal movement so that it, along with attached plate 500, remains in the position illustrated FIG. 31. The extra, post delivery distal motion of guide sleeve 512 is used to reset the dose indicators automatically at the end of each delivery stroke as will be described below.

Cartridges 478, 480 include pistons 526, 528 mounted within the barrels 530, 532 of cartridges 478, 480. Cartridges 478, 480 include liquid pharmaceuticals 534, 536 housed within the interiors of barrels 530, 532 between pistons 526, 528 and septums 484.

Pistons 526, 528 are driven by stems 538, 540 having external threads 542 formed thereon. Stems 538, 540 extend into the hollow interiors of dose screws 544, 546. Dose screws 544, 546 have segmented distal ends 548, 550 with internal threads 552 formed therein. Dose screw 544 is shown in more detail in FIGS. 33 and 36A.

Distal ends 548, 550 are normally dilated somewhat so that stems 538, 540 can slide freely within dose screws 544, 546 without internal and external threads 552, 542 engaging. To caused threads 552, 542 to engage, a dual locking collar 554 having a pair of bores 556 formed therein is used. That is, positioning collar 554 over distal ends 548, 550 squeezes the segmented distal ends over the stems 538, 540 causing threads 542, 552 to engage. The procedure for making this occur is discussed below with reference to FIGS. 35 and 36A-36C.

Cartridges 478, 480 are housed primarily within cartridge bores 558, 560 formed through manifold housing 406. The proximal ends 562, 564 of cartridges 478, 480 extend into cartridge bore extensions 566, 568 formed in drive housing 514. Manifold/cartridge/accumulator assembly 424 is mounted to body 404 by inserting assembly 424 through the open distal end 570 of manifold housing 406. Manifold housing 406 includes a rocker 572 pivotally secured within a cutout 574 formed in manifold housing 406 by a pivot pin 576. See FIGS. 30 and 36A-36C. A rocker spring wire 578 is mounted in a bore 580 formed in manifold housing 406 and extends into cutout 574 so that spring wire 578 engages the inner surface 582, see FIG. 35 of rocker 572 to pivotally bias rocker in the direction opposite of arrows 584 of FIG. 35.

Figure 35:
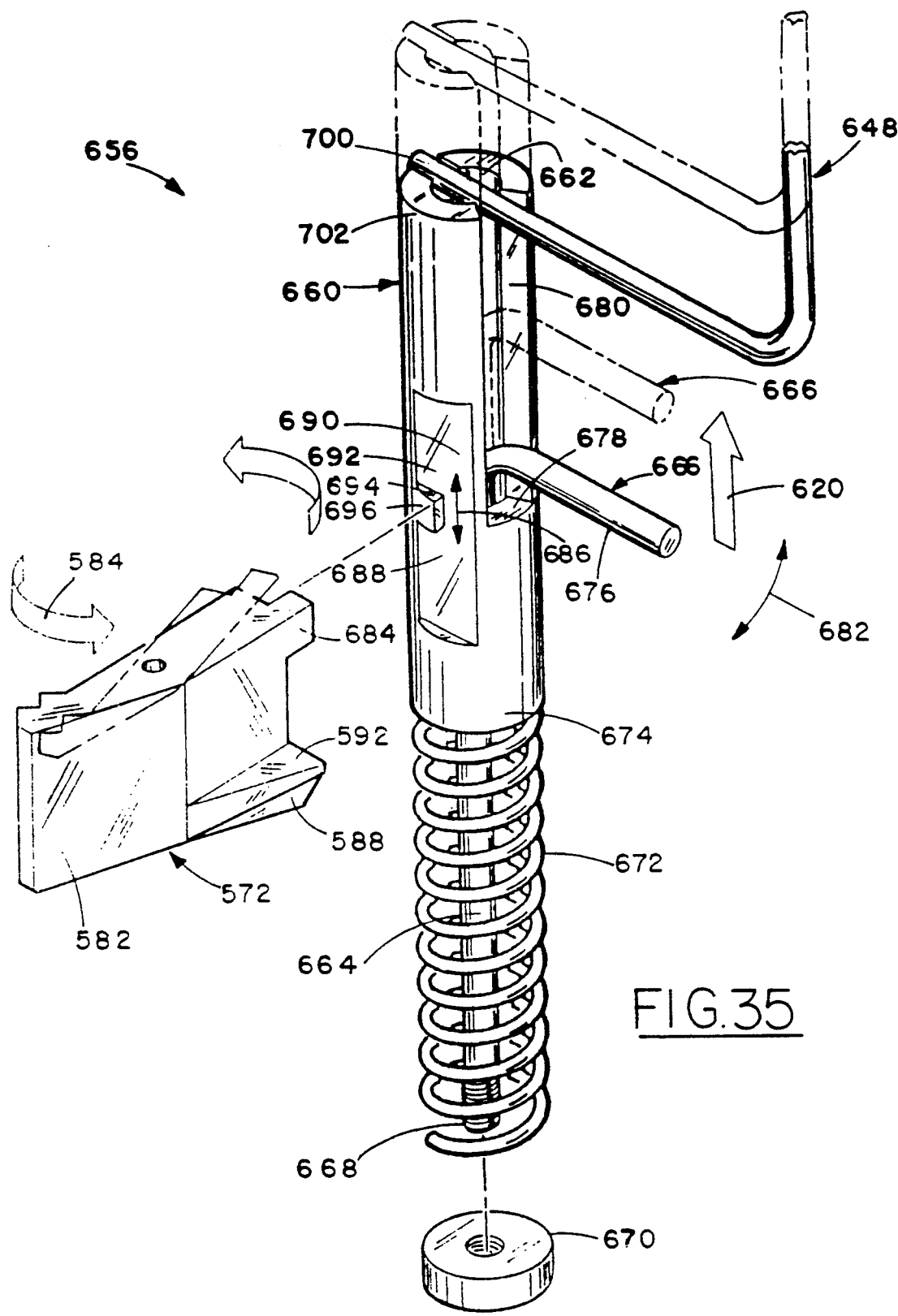
FIG. 35 is an enlarged isometric view of the shift delay assembly, the distal end of the shift link and the rocker of FIG. 30 illustrating the pivotal movement of the rocker and the proximal axial movement of the delay link of the shift delay assembly to dashed line positions during insertion of the manifold/cartridge/accumulator assembly with the shift delay tab of the rocker engaging the shift delay stop of the shift delay cylinder which keeps the shift delay cylinder in the solid line position of FIG. 35, so that after the manifold/cartridge/accumulator assembly is fully seated within the body, the rocker pivots back to the solid line position which permits the shift delay spring to drive the shift delay cylinder and shift link to the dashed line position to cause the dual locking collar to move proximally over the previously dilated distal ends of the dose screws causing the internal threads on the dose screws and the external threads on the stems to engage.

The movement of assembly 424 into body 404 causes surface 586 of manifold base 456 to engage a caming surface 588, see FIGS. 35, 36A-36C, on rocker 572 thus rotating the rocker in the direction of arrows 584 in FIG. 35 and of against a bias of spring 578. Once an assembly 424 is fully inserted into body 404, edge 590 of manifold cover 426 passes surface 592 of rocker 572 and rocker 572 snaps back into the manifold lock position in the direction of arrows 584, thus capturing assembly 424 in body 404. See FIG. 36C.

Dose screws 544, 546 have external indicator threads 594, 596 formed between distal ends 548, 550 and outwardly extending flanges 598. The portions of dose screws 544, 546 including threads 594, 596 are housed within the bores 600, 602 formed in drive housing 414. Flanges 598 are captured between proximal end 422 of drive housing 414 and distal end 604 of dose knob housing 420. Dose screws 544, 546 can rotate in body 414 but cannot move axially in the body. Dose screws 544, 546 include dose knob extensions 606 over which axially extending dose knobs 608 are telescopically mounted. As shown in more detail in FIGS. 32A and 32B, dose knob springs 610 are mounted within interiors 612 of dose knobs 608. The axial, telescoping travel of dose knobs 608 is limited by a pin 614 which is housed within a lateral bore 616 formed in dose knob 608 and extends into an axially extending slot 618 formed in extension 606.

Figure 29:
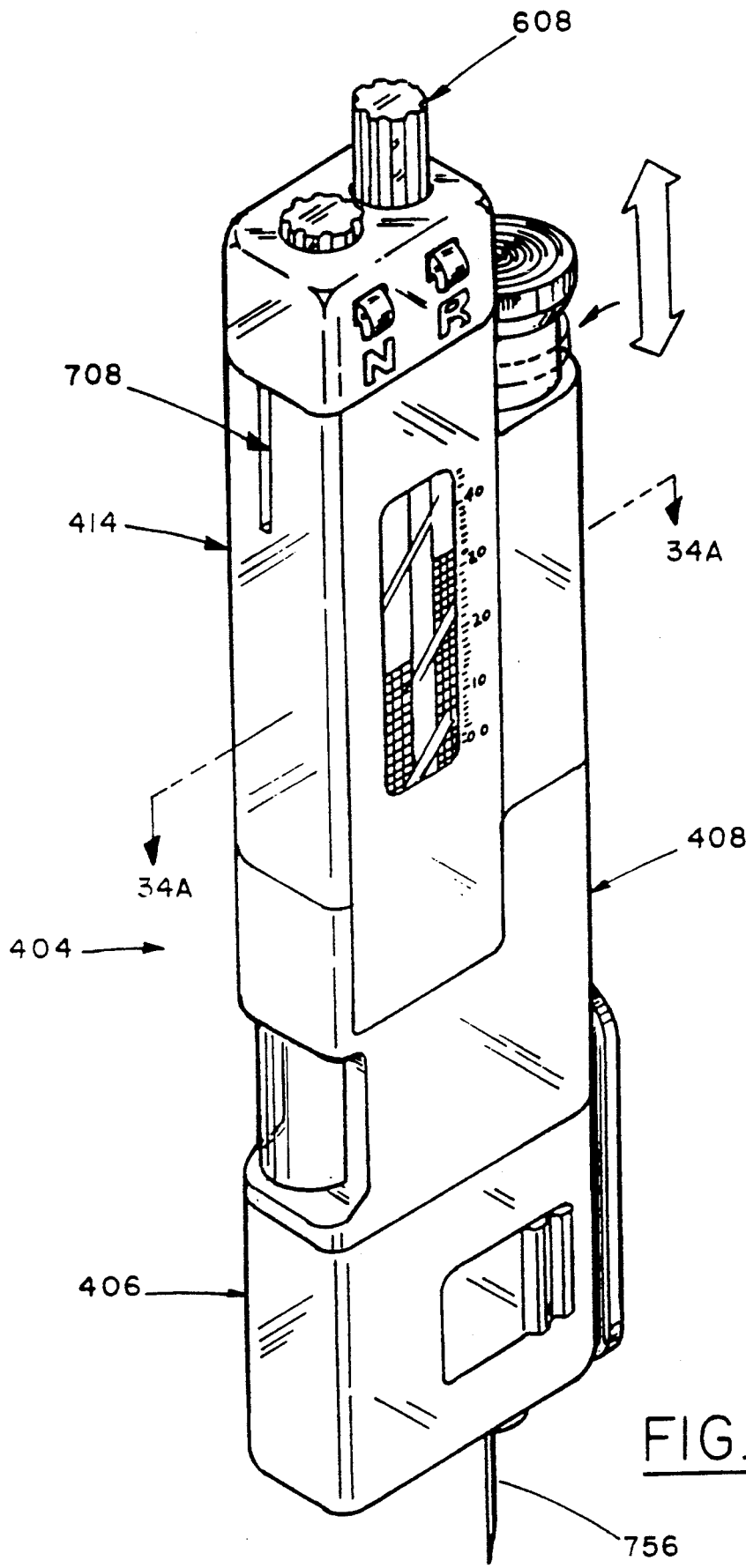
FIG. 29 is an assembled perspective view of an alternative embodiment of the syringe of FIG. 12.
Figure 30:
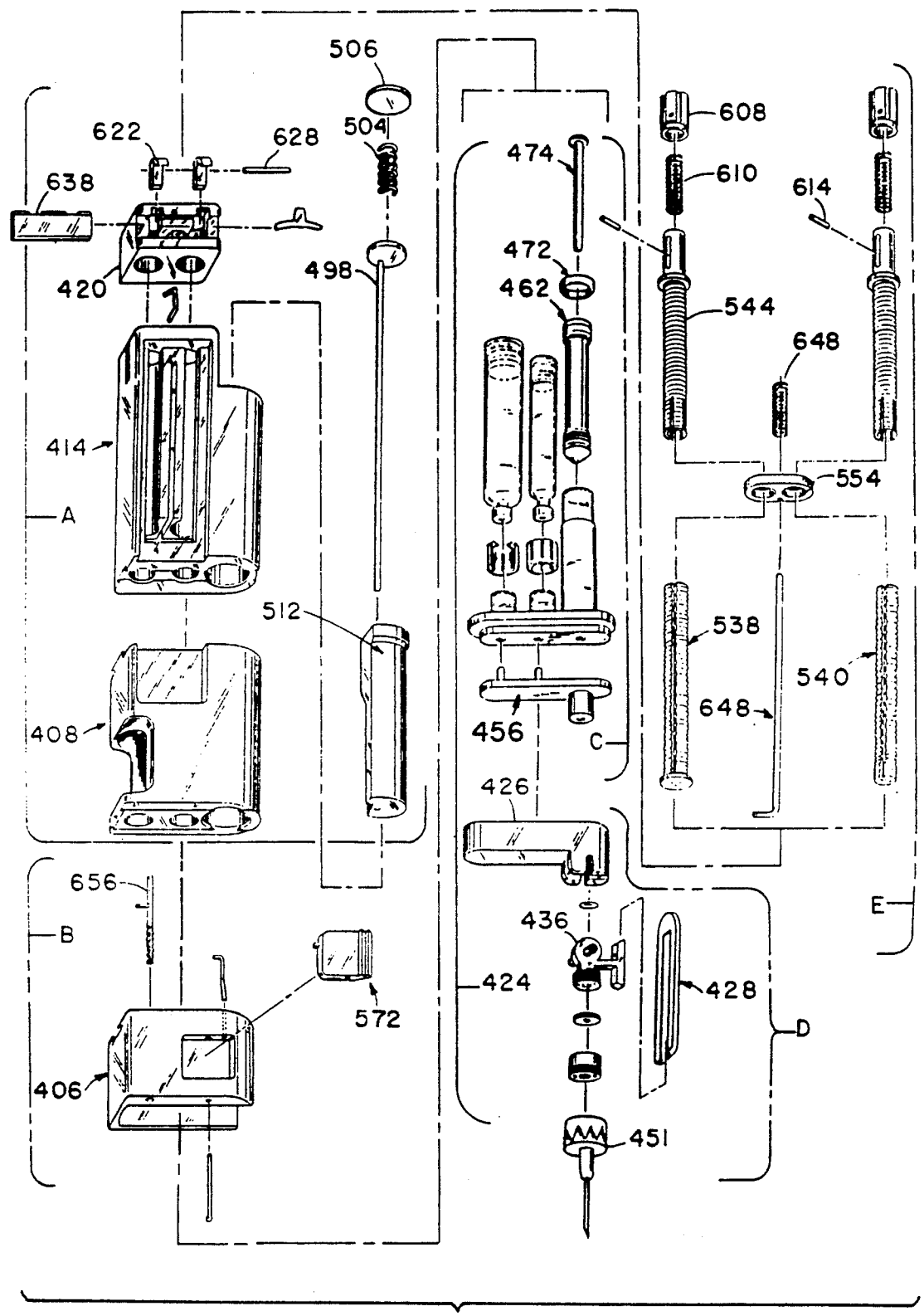
FIG. 30 is an exploded perspective view of most of the component parts of the syringe of FIG. 29, with the exception of the display assembly, shown in FIG. 33.
Figure 30A:
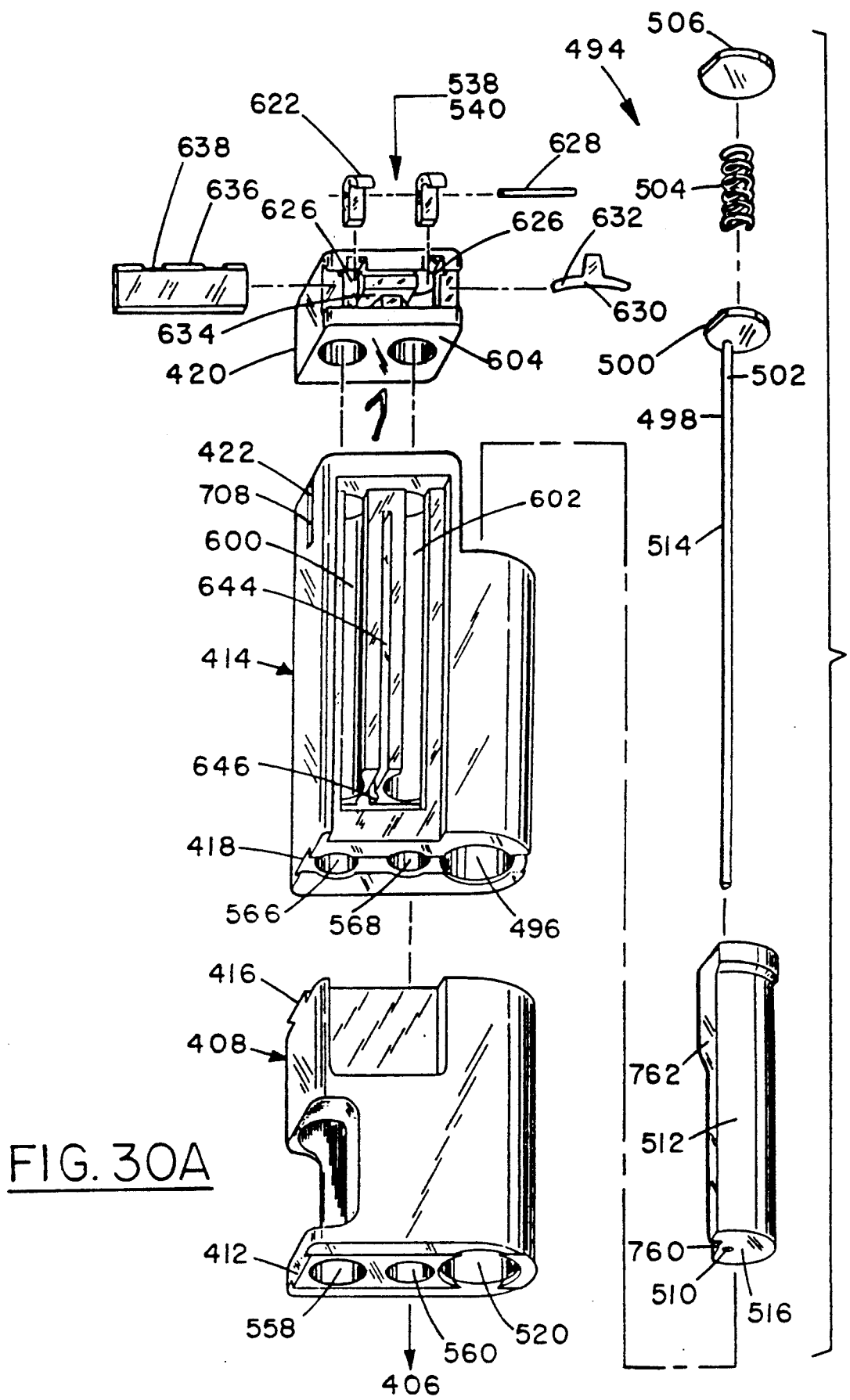
FIG. 30A is an enlarged view of the portion of FIG. 30 designated by A in FIG. 30.
Figure 30B:
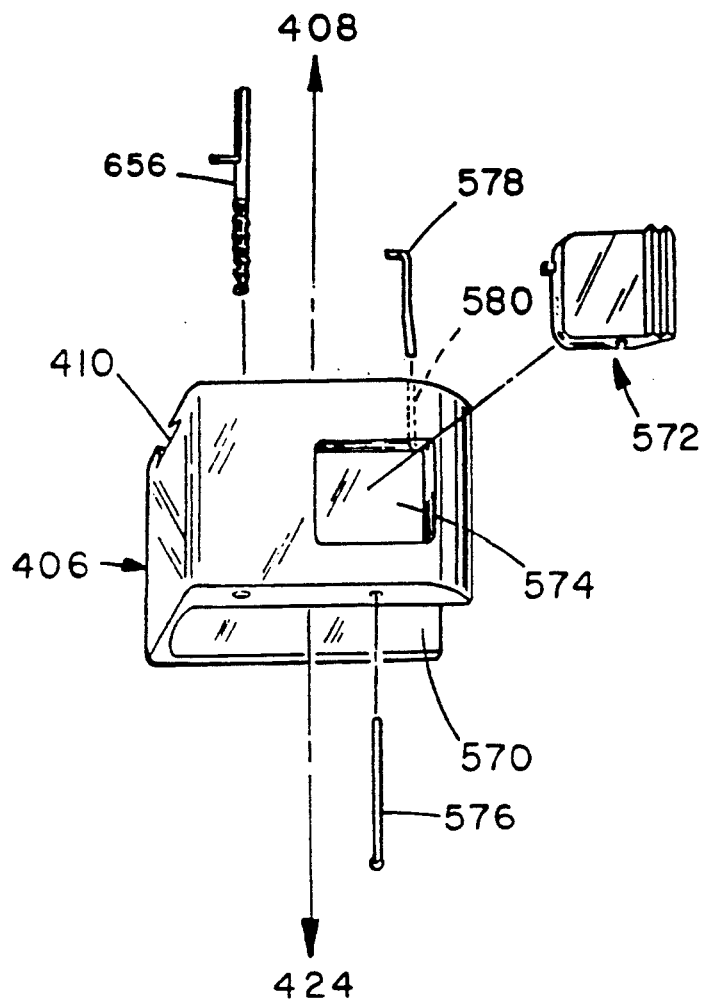
FIG. 30B is an enlarged view of the portion of FIG. 30 designated by B in FIG. 30.
Figure 30C:
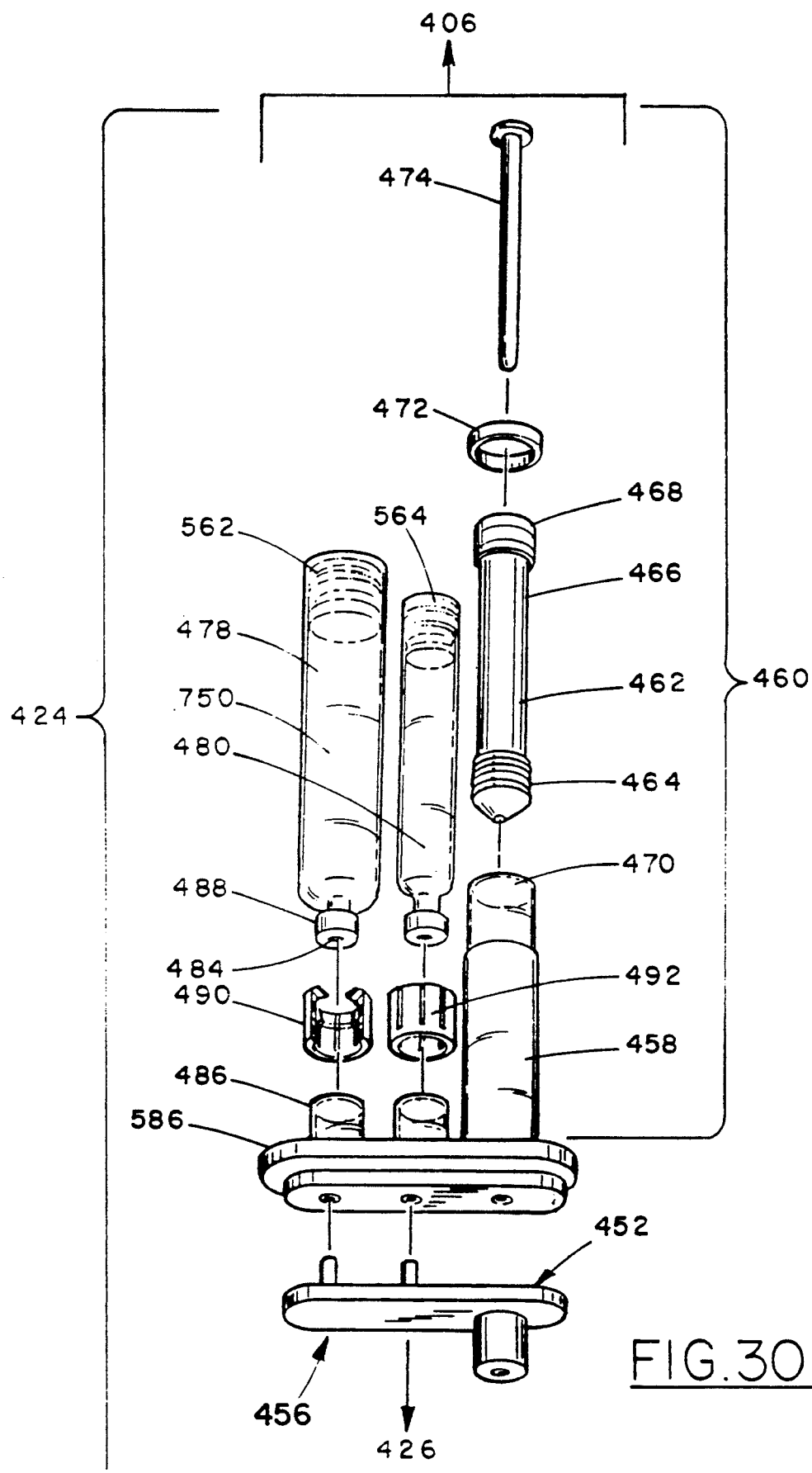
FIG. 30C is an enlarged view of the portion of FIG. 30 designated by C in FIG. 30.
Figure 30D:
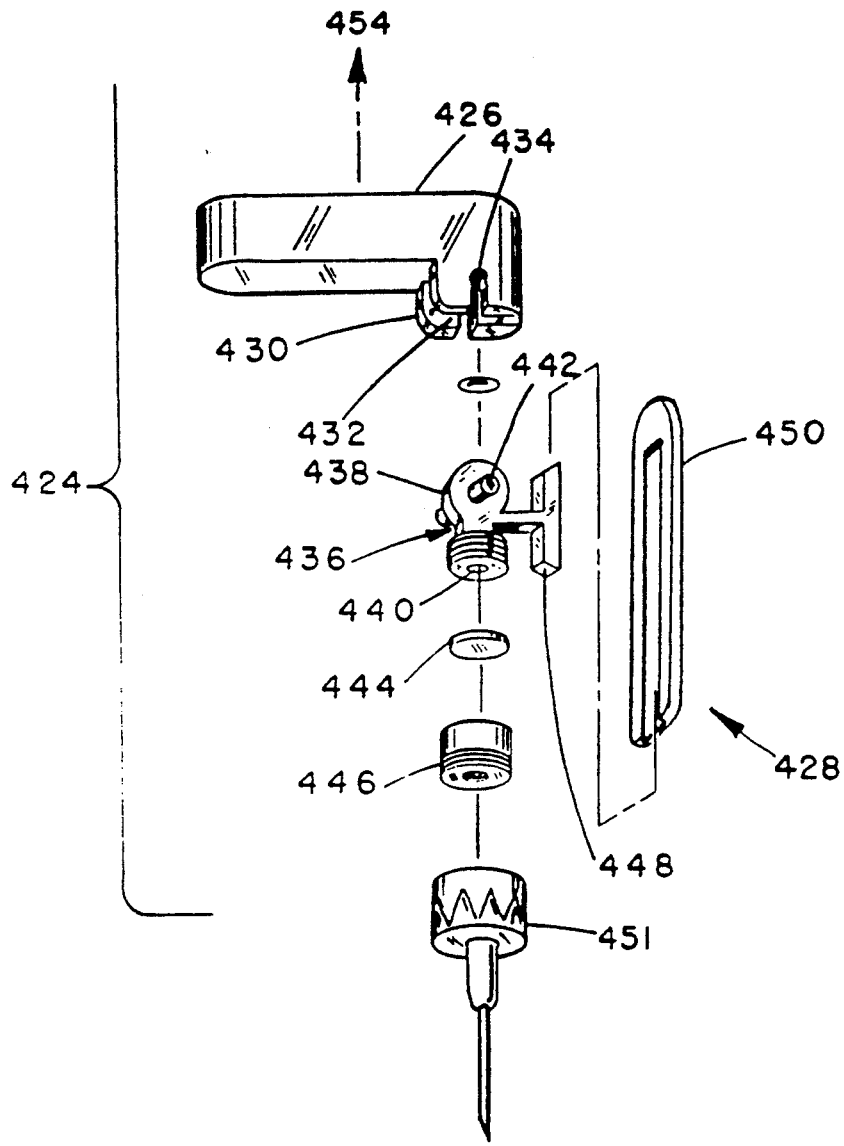
FIG. 30D is an enlarged view of the portion of FIG. 30 designated by D in FIG. 30.
Figure 30E:
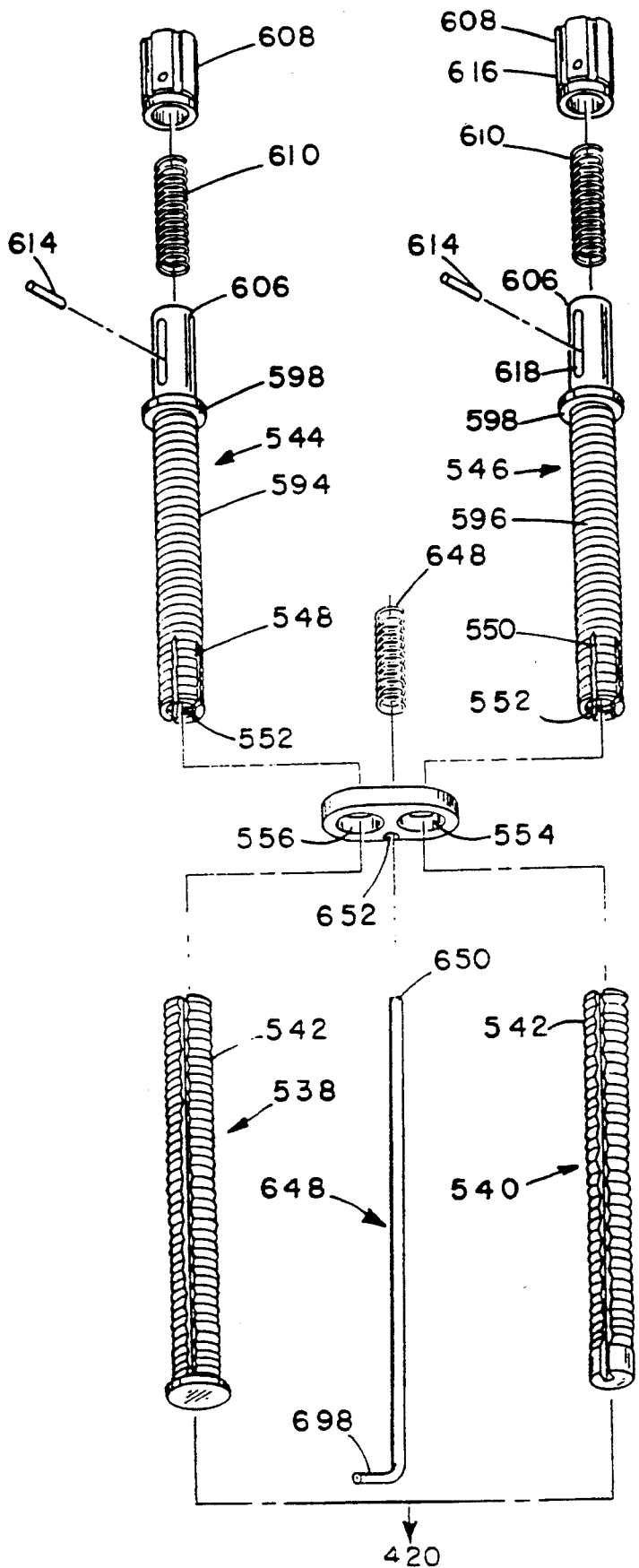
FIG. 30E is an enlarged view of the portion of FIG. 30 designated by E in FIG. 30.
Figure 32A:
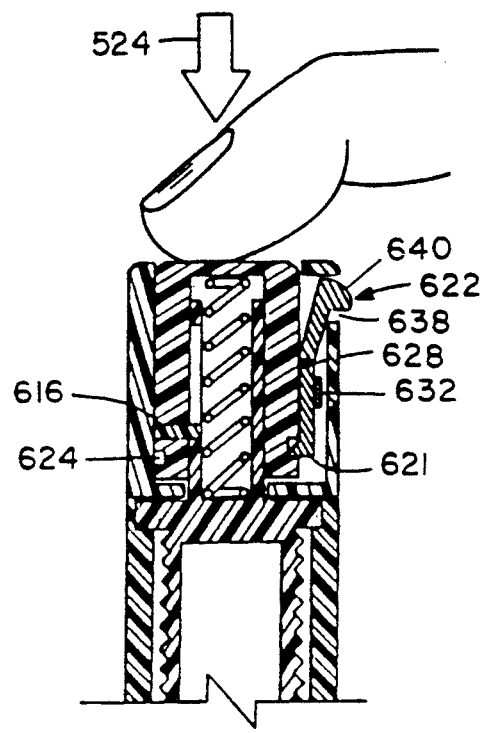
FIGS. 32A and 32B are enlarged cross-sectional views showing movement of the dose knob in the distal direction to the collapsed position in FIG. 32A and the dose knob being released by pressing on the trigger so the dose knob moves in the proximal direction to the extended position in FIG. 32B.
Figure 32B:
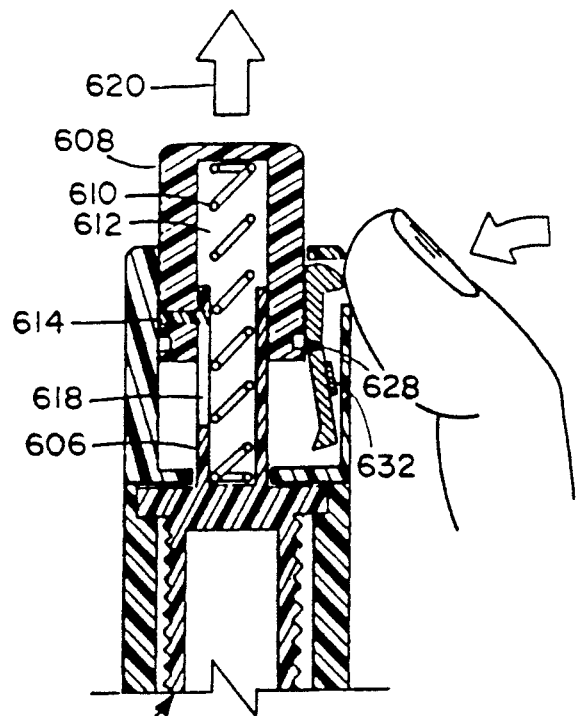

Dose knobs 608, as shown in FIGS. 29, 32A and 32B, can be biased by the user in distal direction 524 to the retracted or collapsed position, see FIG. 32A, or released to move in a proximal direction 620 to an extended position, as shown in FIG. 32B, under the force of compression coil spring 610. Dose knobs 608 are retained in the collapsed position of FIG. 32A by the engagement of a tooth 621 at one end of the trigger 622 within annular groove 624 formed in dose knobs 608. Triggers 622 are pivotally mounted within cutouts 626 formed in housing 420 by a common pivot pin 628. Triggers 622 are normally biased to the engaged position of FIG. 32A, that is biased so that tooth 621 is forced towards dose knobs 608, by a normally bowed, sheet metal spring 630. Spring 630 has a pair of arms 632 which engage triggers 622 forcing tooth 621 of each trigger 622 towards dose knobs 608. Spring 630 is positioned within a central cutout 634 formed in dose knob housing 420 and is maintained in position by a cover plate 636 which covers cutouts 626, 634.

Cover plate 636 has a pair of notches 638 through which user-assessable button portions 640 pass. To release dose knob 608, the user presses on button portion 640 as shown in FIG. 32B which permits tooth 621 to pivot away from dose knob 608 so that tooth 621 disengages annular groove 624 allowing compression spring 610 to force dose knob 608 in proximal direction 620. Dose knob 608 then assumes the extended position to permit the user to adjust the dose easily. However, when dose knobs 608 are in the collapsed positions, syringe 402 is less bulky and inadvertent adjustment of the dose is much less likely.

Figure 31A:
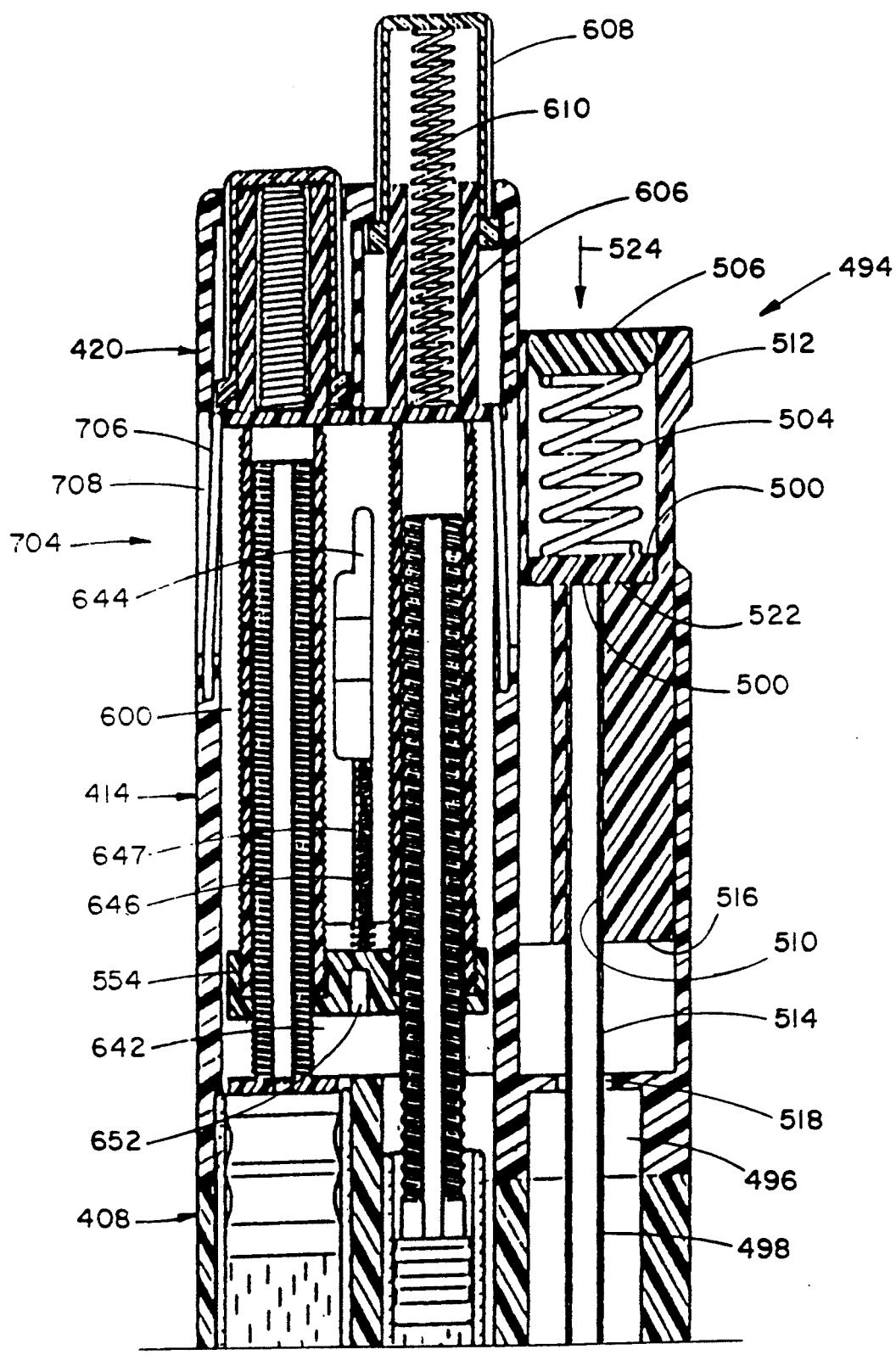
FIGS. 31A and 31B are enlarged proximal and distal portions of the syringe of FIG. 31.
Figure 31B:
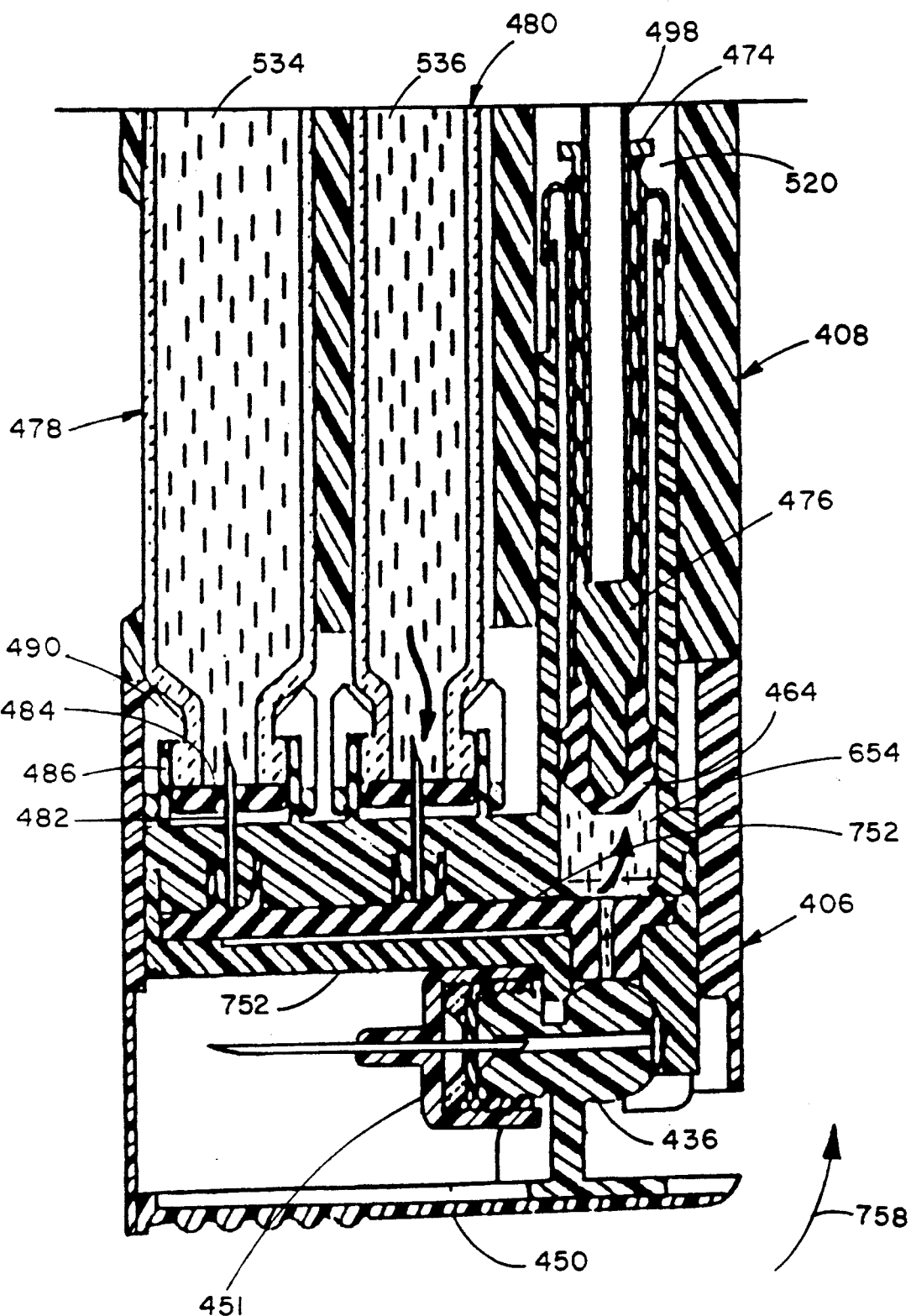

Dual locking collar 554 is housed within an open region 642 formed in drive housing 414. See FIGS. 30 and 31A. Drive housing 414 also includes a longitudinally extending slot or cutout 644 used to guide and house an extension of the display frame as discussed below with reference with FIGS. 33, 34A and 34B. Cutout 644 opens into open region 642. Cutout 644 has an enlarged blind bore 646 within which a light compression spring 647 is housed. Compression spring 647 biases dual locking collar 554 in distal direction 524 to slide off of distal ends 548, 550 of dose screws 544, 546. See FIGS. 36A, 36B. Thus, spring 648 tends to keep dose screws 544, 546 disengaged from stems 538, 540.

Dual locking collar 554 is biased in proximal direction 621 by a shift link 648. Shift link 648, not shown in FIGS. 31 or 31A, has a proximal end 650 which is secured within a hole 652 in collar 554, such as by a press fit or using an adhesive. The action of mounting manifold/cartridge/ accumulator assembly 424 into body 404 drives shift link 648 proximally thus causing dual locking collar 554 to slide over distal ends 548, 550 so that internal and external threads 552, 542 become engaged. See FIGS. 31A, 36B, 36C.

During the installation of assembly 424, which typically includes filled cartridges 478, 480, the distal ends of stems 538, 540 engage pistons 562, 564. Since collar 554 is moved in distal direction 524 by spring 648 off of distal ends 548, 550, stems 538, 540 can move freely within dose screws 544, 546. Thus, the act of installing a new assembly 424 in body 404 moves stems 538, 540 proximally back to beginning positions. However, without some sort of delay mechanism for shifting collar 554, the final axial movement of assembly 424 into body 404 could cause collar 554 to begin to engage distal ends 548, 550 before the end of the movement of assembly 424. This could cause the engagement of external and internal threads 542, 552 before assembly 424 was completely seated. In some cases this could result in difficulty in completely mounting assembly 424 into body 404 or the flow of liquid pharmaceuticals 534, 536 from cartridges 478, 480 into an accumulator chamber 654 defined by accumulator barrel 458 and accumulator piston 464. To prevent this from occurring, a shift delay assembly 656, mounted within a bore 458 in manifold housing 406 is used in conjunction with shift link 648 and rocker 572.

As discussed above, rocker 572 is shown in solid lines in FIG. 35 as it is normally biased by spring 578. Shift delay assembly 656 includes a shift delay cylinder 660 having a central bore 662 through which one leg 664 of an L-shaped delay link 666 passes. Leg 664 has a threaded end 668 onto which a threaded nut 670 is secured. Nut 670 captures a compression coil shift delay spring 672 between a distal end 674 of cylinder 660 and nut 670. Spring 672 is strong enough to normally bias the shorter leg 676 of delay link 666 against the base 678 of a longitudinally extending slot 680 formed in cylinder 660.

Slot 680 is wide enough so that shorter leg 676 of delay link 666 can pivot back and forth in the direction of arrow 682 over an arc of about 15 degrees. Leg 676 is sized and positioned to fit between cartridges 478, 480 but not between collars 490, 492. Leg 676 therefore engages the proximal edges of adapter collars 490, 492 when both cartridges 478, 480, together with their adapter collars 490, 492 are mounted to manifold base 456. See FIGS. 36B, 36C. When one or both of cartridges 478, 480 are not so mounted, or if one or both of collars 490, 492 is missing, delay link 666 will not be driven in proximal direction 621. If only one of the two collars 690, 692 is present, leg 676 will freely pivot out of the way of the collar 490, 492 which is present so that delay link 666 stays in the solid line position of FIG. 35.

Figures 36A, 36B, 36C:
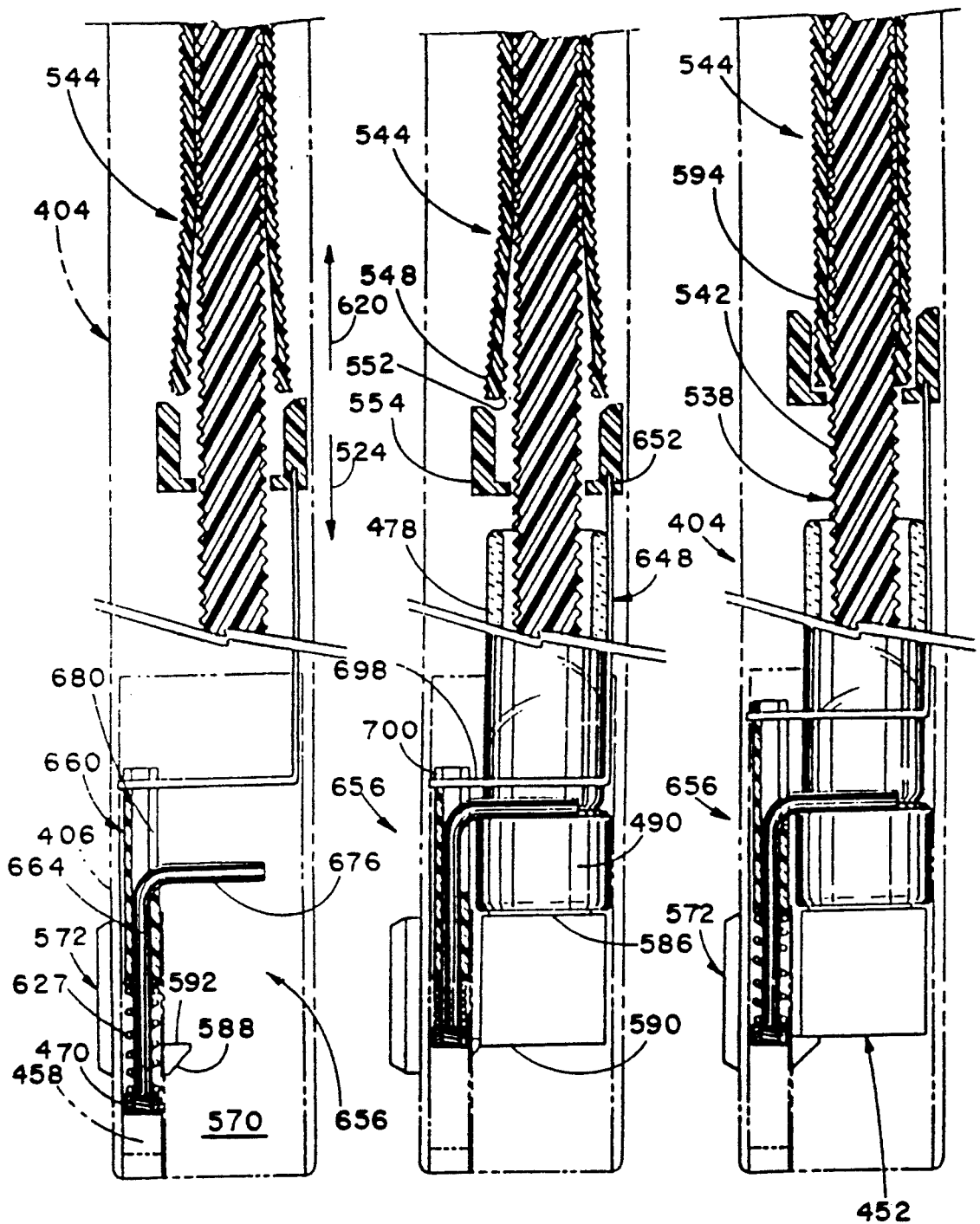
FIGS. 36A, 36B and 36C are simplified, partial cross-sectional views illustrating the operation of the shift delay assembly of FIG. 35 as the manifold/cartridge/accumulator assembly is removed from the body in FIG. 36A, almost completely inserted into the body in FIG. 36B and completely inserted into the body in FIG. 36C, the shift link moving proximally, thus driving the dual locking collar over the dose screw, only after the final movement to the completely inserted position of FIG. 36C.

With rocker 572 in the solid line position of FIG. 35, the shift delay tab 684 will be able to move freely along an axial path 686 within a cutout region 688 formed in cylinder 660. However, when rocker 572 is pivoted in the direction of arrows 584, see FIGS. 35 and 36B, as occurs during the final motion of insertion of assembly 424 into body 404, shift delay tab 684 moves from position 690 along path 686 to a position 692 directly opposite a proximally-facing face 694 of a shift delay stop 696 carried by shift delay cylinder 660. When so positioned, shift delay tab 684 prevents any substantial movement shift delay cylinder 660 in a proximal direction 621. Thus, as assembly 424 continues to be moved into body 404, and assuming cartridges 478, 480 and their associated adapter collars 490, 492 are mounted thereto, movement of delay link 666 in proximal direction 621 will simply compress spring 672 moving shorter leg 676 away from faces 678 until shorter leg 676 assumes the dashed line position of FIG. 35 and the position of FIG. 36B. During this motion from the solid line to the dashed line positions of delay link 666, corresponding to FIGS. 36A and 36B, the distal end 698 of shift link 648 is maintained in the same position within a short slot 700 at the proximal end 702 of shift delay cylinder 660. Only after manifold/cartridge/accumulator assembly 424 is fully mounted within body 404, as shown in FIG. 36C, can rocker 572 pivot back to the solid line position of FIG. 35, thus moving shift delay tab 684 from position 692 to position 690. Doing so allows compressed spring 672 to drive shift delay cylinder 660 from the solid line position of FIG. 35 to the dashed line position of FIG. 35, thus driving shift link 648 in proximal direction 620 therewith. This movement can be seen by comparing FIGS. 36B and 36C. The shift link 648 movement occurs after all movement of assembly 424 is completed, and thus after all movement of stems 538, 540 within dose screws 548, 546 is completed as well. In the position of FIG. 36C, shift link 648 thus causes dual locking collar 554 to reengage over distal ends 548, 550, thus causing reengagement of threads 542, 552.

Figure 33:
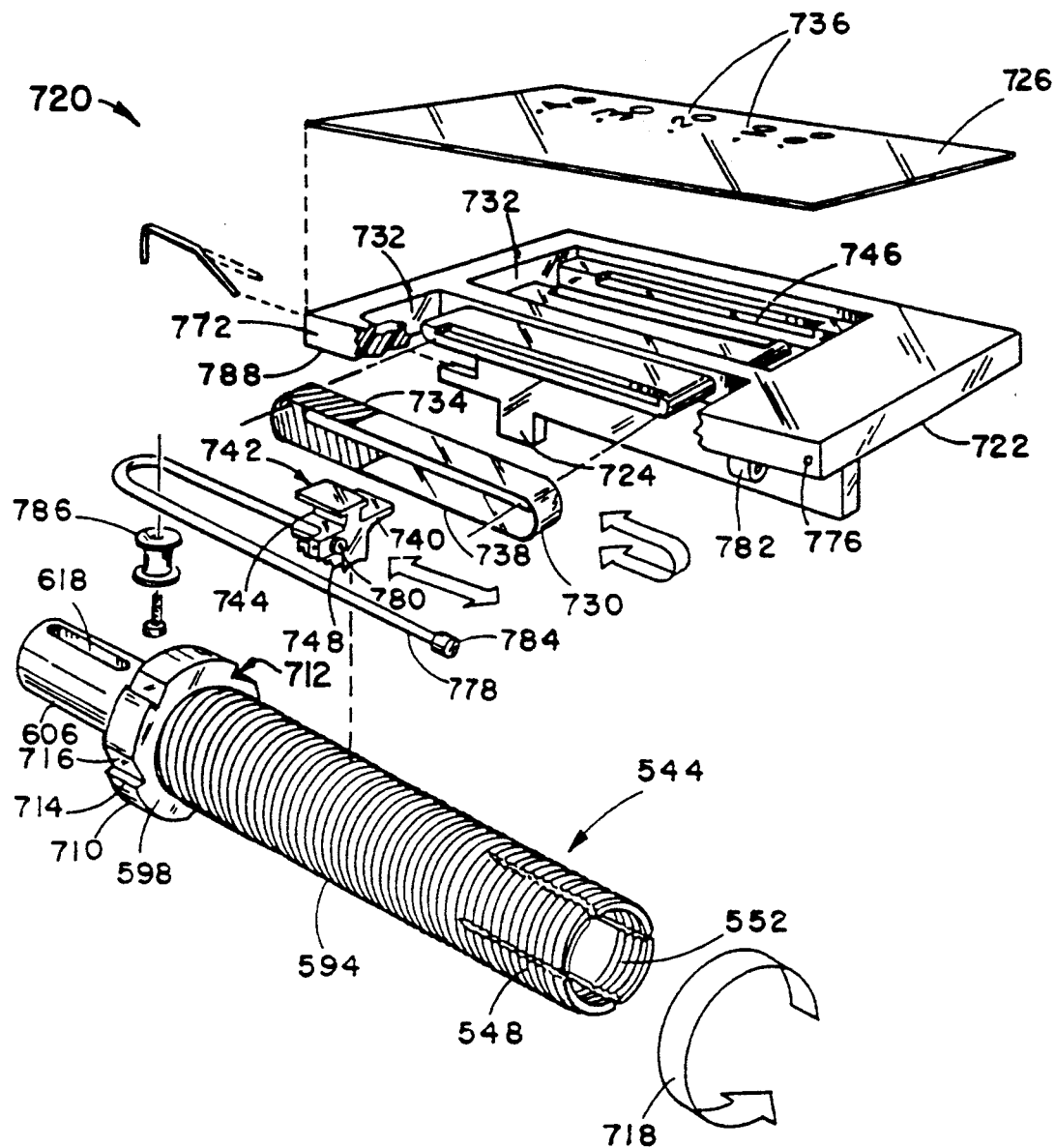
FIG. 33 is a somewhat simplified exploded perspective view of the display assembly overlaying one of the dose screws.

FIGS. 26-28 illustrate a rotary ratcheting mechanism for syringe 160. Syringe 402 has a similar ratcheting mechanism 704, as shown in FIGS. 31 and 33. Mechanism 704 includes a ratchet wire 706 mounted within axially extending slot 708 formed in drive housing 414. Ratchet wire 706 engages a notched outer circumference 710 on flange 598 of dose screw 44. Ratchet wire 706 rides along notched surface 710 and provides an audible and tactile indication of the rotation of dose screws 544, 546. Each notch 712 has a radially extending surface 714 and a tapered surface 716 which prevents rotation of dose screw 544 in the wrong direction, that is opposite arrow 718 in FIG. 33.

Figure 23:
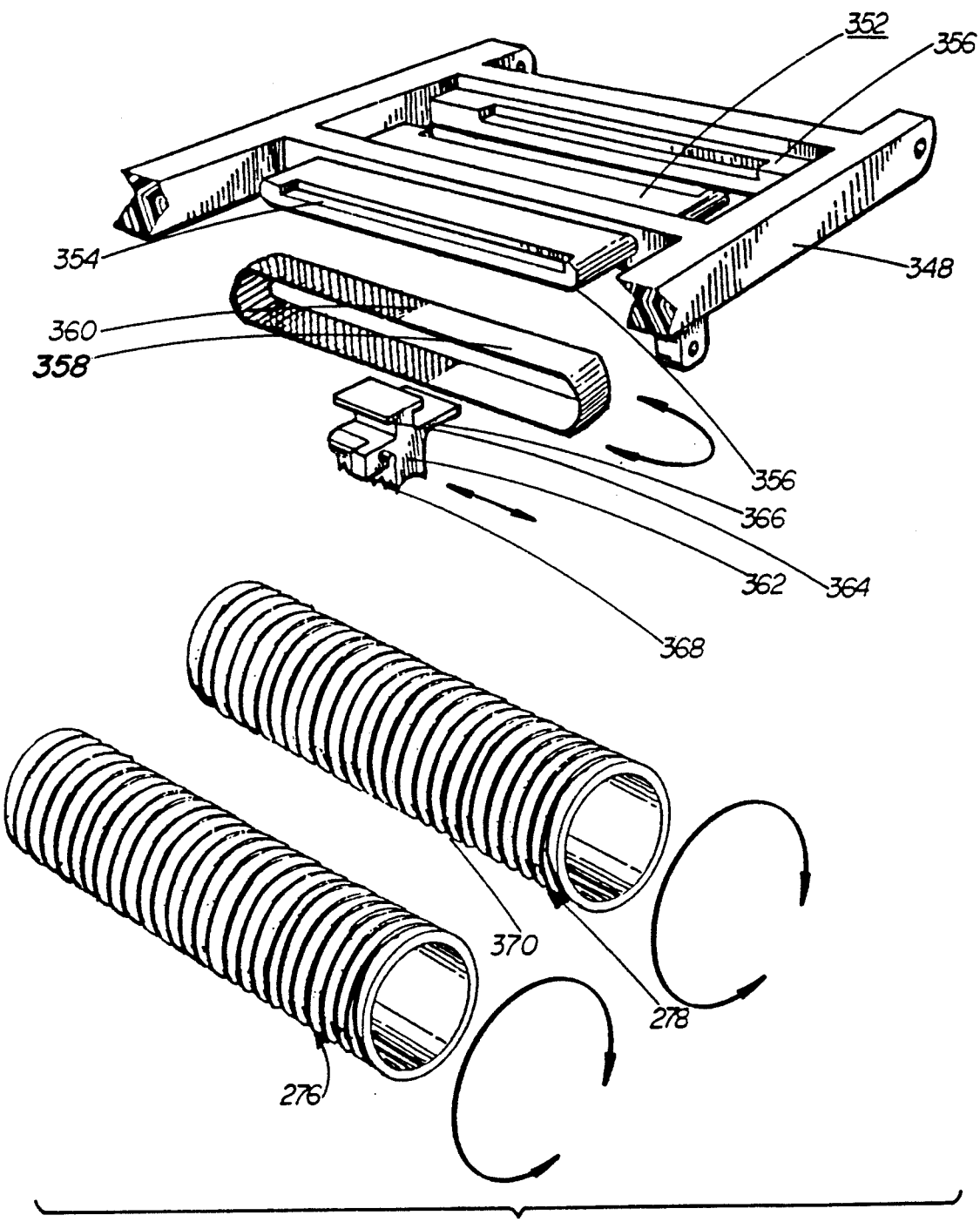
FIG. 23 is a simplified exploded isometric view of a portion of the optical dose indicator of FIG. 13A together with associated stem drivers.
Figure 24:
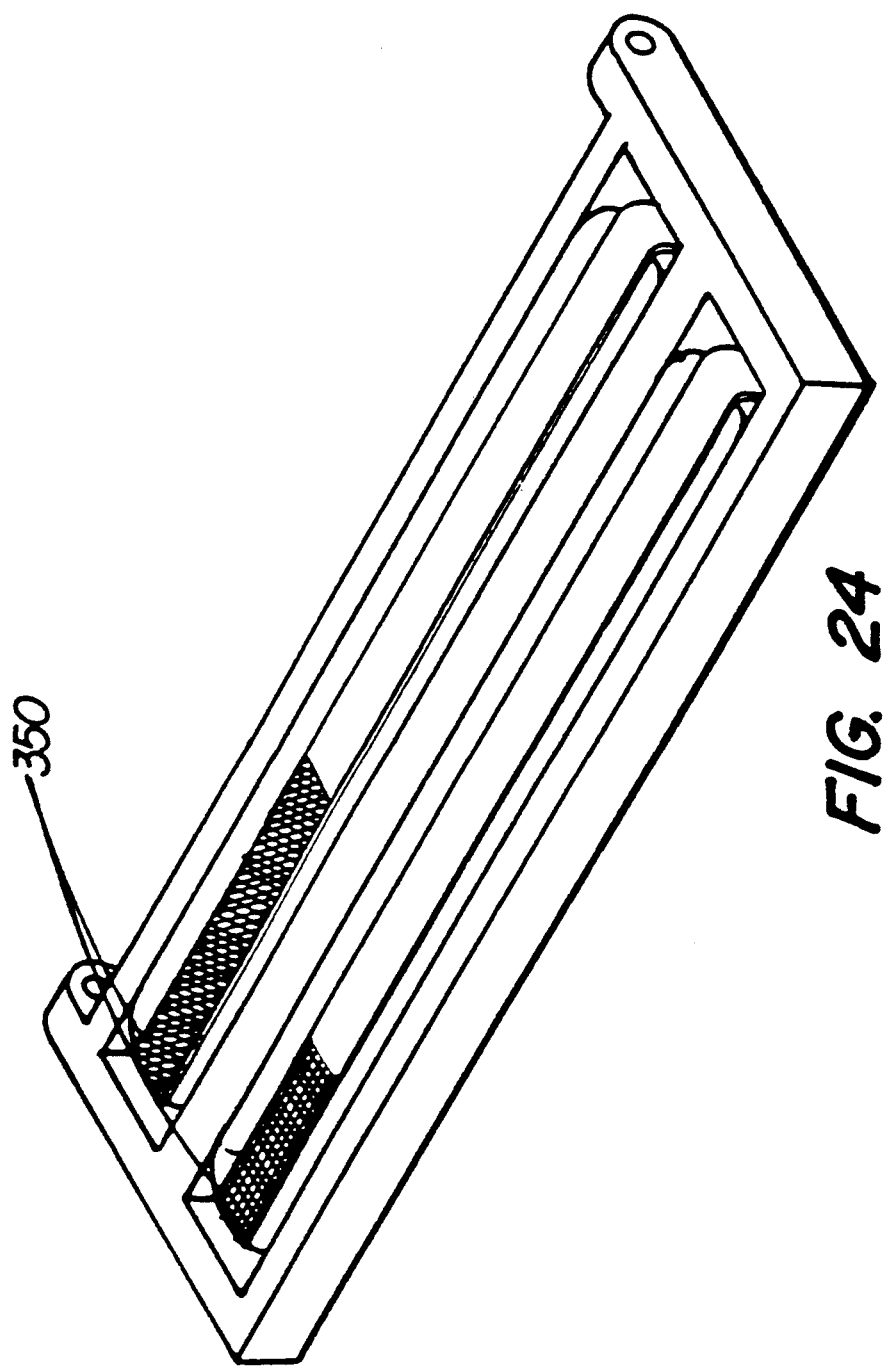
FIG. 24 shows the frame, indicator ribbons and followers of FIG. 23 in an assembled condition.
Figure 25:
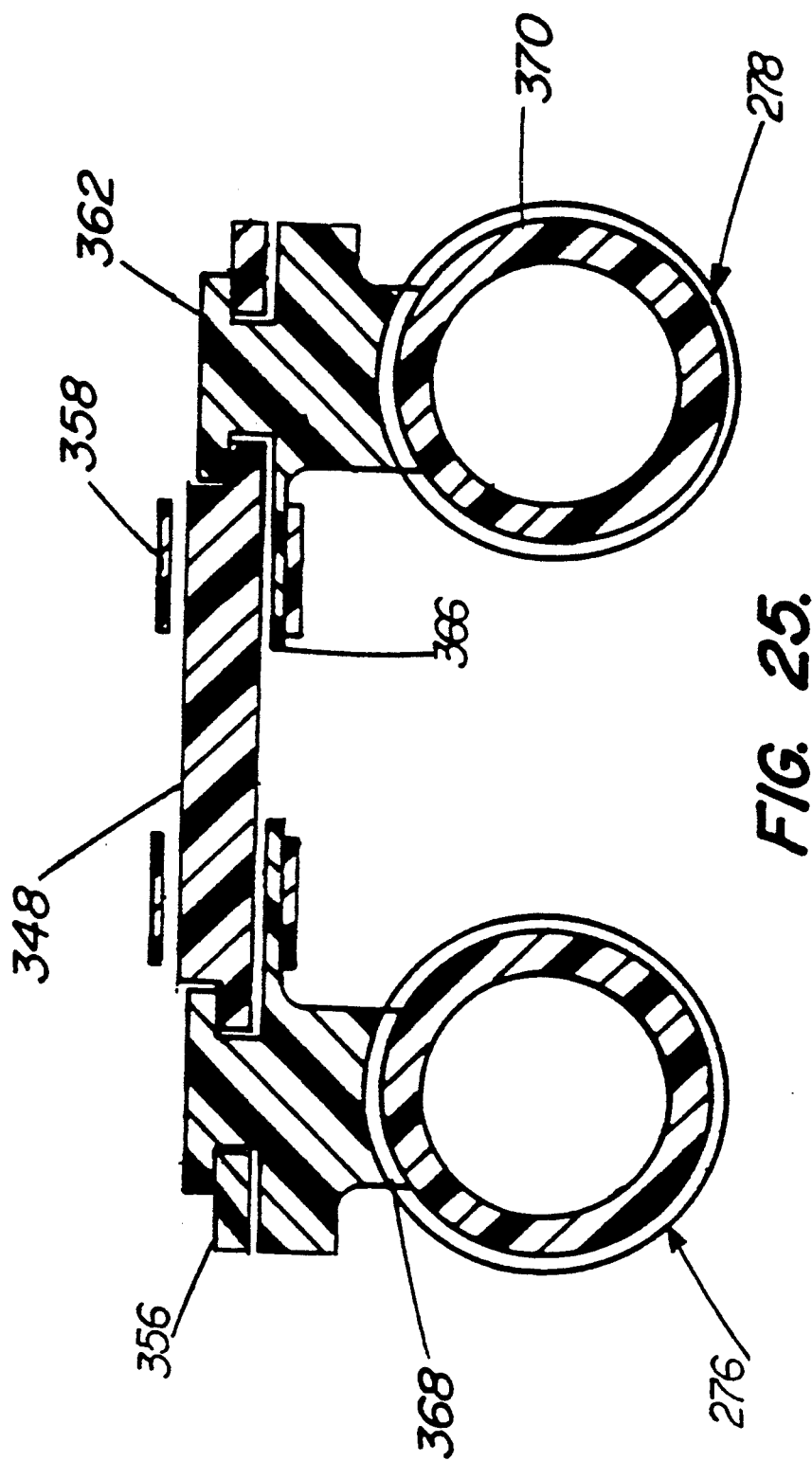
FIG. 25 is a simplified cross-sectional view showing the structure of FIG. 24 engaging associated stem drivers.
Figure 34A:
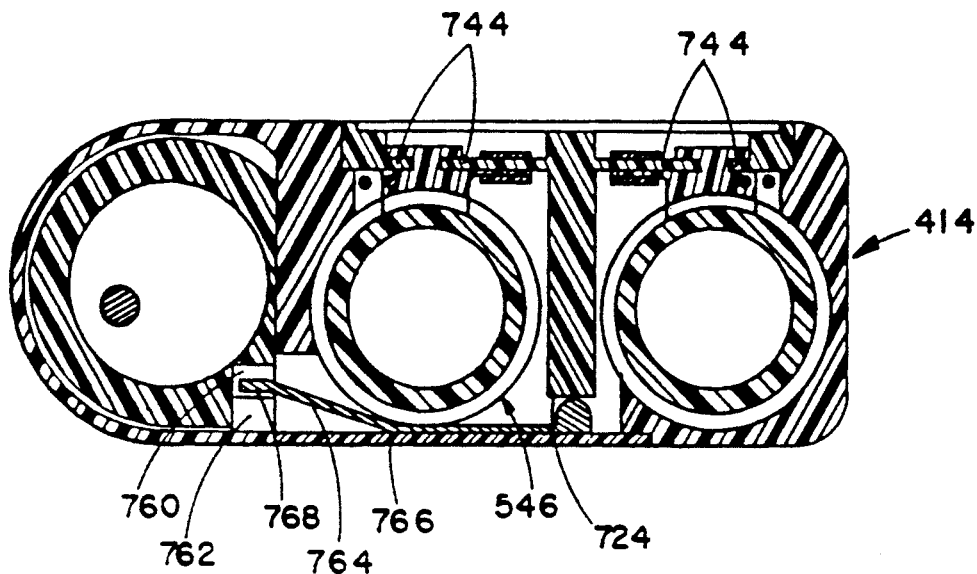
FIGS. 34A and 34B show a cross-sectional view taken through the syringe of FIG. 29 along line 34A—34A with the accumulator stem assembly in the solid line position of FIG. 31 so that the dose followers remain engaged with the dose screws and the window of the display assembly remains coplanar with the surface of the body.
Figure 34B:
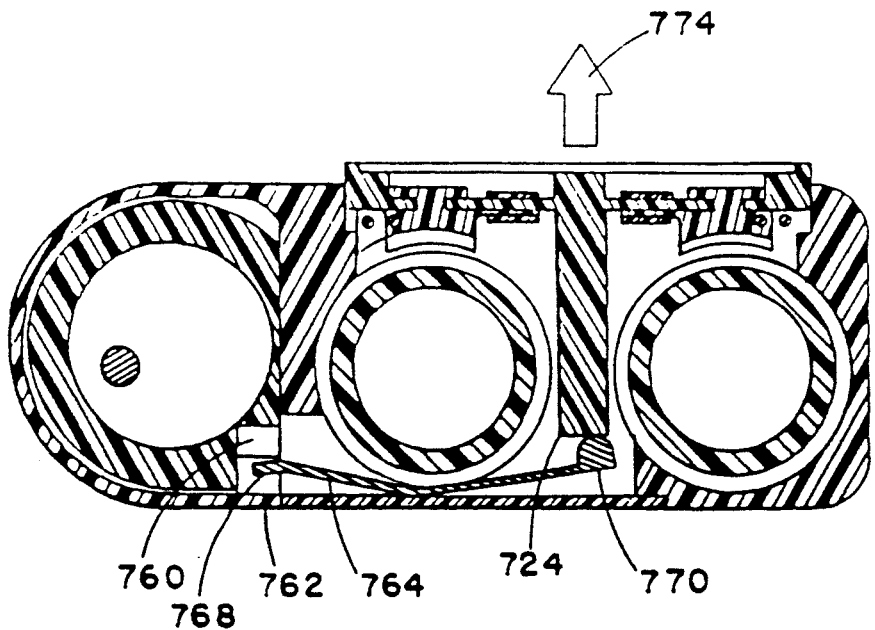

FIGS. 33, 34A, and 34B illustrate a pop-up display assembly 720 similar to the display assembly shown in FIGS. 23-25. Display assembly 720 includes a display frame 722 having a frame extension 724 which is housed within cutout 644 formed in housing 414. Display assembly 720 includes a display window 726 mounted to the outer surface 728 of display frame 722. Window 726, as suggested in FIG. 29, is clear over a central portion and is opaque along its borders. The clear portion of window 726 permits the user to view indicator ribbons 730 as they move within support region 732 of display frame 722. Indicator ribbons 730 each include a line of demarcation 734 to indicate the amount of the liquid pharmaceutical being dispensed. The amount is quantified using numerical indicia 736 printed on window 726.

A lower reach 738 of ribbon 730 is secured to a gripping portion 740 of a follower 742. Follower 742 has a pair of slots 744 which engage guide surfaces 746 within support region 732. Follower 742 includes teeth 748 which normally engage similarly configured external threads 594 on dose screw 544. As dose screw 544 is rotated, thus driving stem 538 against piston 562, the amount of liquid pharmaceutical 534 driven from cartridge 478 along a flow path 752 and into accumulator chamber 654 is shown by the location of line of demarcation 734, as viewed through window 726. As liquid pharmaceutical 534, 536 from each of the cartridges 478, 480 is driven into accumulator chamber 654, accumulator stem assembly 494 moves in a proximal direction 525. To prepare for making the injection, the user slides a plate 450 in the direction of arrow 754 to both expose needle 756 and provide the user with a significant mechanical advantage in pivoting needle mount assembly 428 in the direction of arrow 758. A needle assembly 451, assuming one is not already mounted to assembly 428, is then mounted to septum cap 446. The injection is then given by pressing on accumulator stem assembly 494 in distal direction 524, thereby forcing accumulator piston 464 in distal direction 524 to expulse the mixed pharmaceutical.

At the end of the delivery stroke, that is with accumulator stem assembly 494 in the solid line position of FIG. 31, the user can continue pressing in distal direction 524 to compress spring 504 and move accumulator guide sleeve 512 in the same direction. Accumulator guide sleeve 512 includes an axially extending recess 760 extending from distal end 516 of accumulator guide sleeve 512. Recess 760 has a rocker arm cam surface 762 at one end. A rocker cam follower 764, see FIG. 34A, is captured between dose screw 546 and the rear wall 766 of drive housing 414. Follower 764 has a cam contact portion 768 which, during the movement of accumulator stem assembly 464 between the solid line and dashed line positions of FIG. 29, lies within recess 760. However, at the end of a delivery stroke, if the user continues to press on accumulator stem assembly 494, portion 768 rides up on rocker arm cam surface 762, as illustrated in FIG. 34B. Doing so causes rocker cam follower 764 to pivot in a counterclockwise direction in FIG. 34B, driving display frame extension contact portion 770 against frame extension 724 to lift the proximal end 772 of display frame 722 away from body 404, as indicated by arrow 774 in FIG. 34B. This causes frame 722 to pivot about pivot points 776, thus raising followers 742 away from dose screws 544, 546, so that teeth 748 disengage teeth 594, 596. This permits an elastic band 778, secured to follower 742 at one end 780 and to an anchor point 782 on display frame 722 at the other end 784, to automatically pull indicator ribbon 730 so that line of demarcation 734 returns to its initial or zero position. Elastic band 778 passes about a guide pulley 786, the guide pulley being secured to the underside 788 of display frame 722 adjacent proximal end 772 of the display frame.

Display assembly 720 is designed so that the dose indicators automatically return to a start or zero position at the end of a dispensing procedure. If desired, the resetting of display assembly 720 could be accomplished manually, such as by using a push-button extending from rear wall 766 of drive housing 414.

Other modification and variation can be made to the disclosed embodiments without departing from the subject of the invention as defined in the following claims. For example, syringe 2 could be modified so that an empty, generally conventional cartridge is used as accumulator chamber 10. The needle assembly could be permanently mounted in place. Instead of using check valves 58, 59, pistons 42, 44 could be made to be movable in one direction only, towards far end 38, to prevent the reverse flow of liquid back into the cartridges. The syringe could be made for use with more than two cartridges. The liquid in the accumulator chamber could be dispensed using something other than a piston, such as by rolling up a collapsible bag or collapsing a bellows. The invention could dispense the liquid from the accumulator chamber using something other than a hollow needle, such as a needless injector or through an IV line. The invention may also include an additional cartridge or chamber containing sterile saline solution useful for flushing out the hollow needle and fluid pathway downstream of the spikes after an injection. Instead of shift delay assembly 656, a viscous damped spring assembly could be used to delay the axial movement of shift link 648 from the position of FIGS. 36A and 36B to the position of FIG. 36C.

What is claimed is:

1. A pharmaceutical dispenser comprising:
   at least two pharmaceutical cartridges each having a barrel, the barrel having a cartridge interior, an open end and an accessible end, a piston within the barrel and a liquid within the cartridge interior between the piston and the accessible end;
   a body configured of house the cartridges therein;
   an accumulator/dispensing assembly mounted to the body and including an accumulator chamber fluidly coupled to the cartridge interiors;
   means for selectively driving amounts of the liquids within the cartridge interiors into the accumulator chamber; and
   the accumulator/dispensing assembly including means for dispensing liquid from the accumulator chamber.

2. A pharmaceutical dispenser comprising:
   at least two pharmaceutical cartridges each having a barrel, the barrel having a cartridge interior, an open end and an accessible end, a piston within the barrel and a liquid within the cartridge interior between the piston and the accessible end;
   a body configured to house the cartridges therein;
   an accumulator/dispensing assembly mounted to the body and including an accumulator chamber fluidly coupled to the cartridge interiors;
   a piston driver for each said cartridge mounted to the body, the piston drivers each including a movable stem driver having a longitudinal axis and a stem, the stem driver including a stem drive element, the stem having a proximal end and a distal end which engages the piston, the stem drive element drivingly coupled to the stem so that movement of the stem drive element determines the amount of axial movement which is applied to the stem, and thus the piston, by the stem drive element so to determine how much of the liquid within the cartridge interior is forced into the accumulator chamber;
   the accumulator/dispensing assembly including means for dispensing liquid from the accumulator chamber; and
   each stem driver including:
      a telescoping knob axially slidably mounted to the proximal end of the stem drive element to be movable in a proximal direction from a collapsed position to an extended position and in a distal direction from the extended position to the collapsed position;
      means for biasing the knob in the proximal direction;
      means for retaining the knob in the collapsed position; and
      means for manually releasing the retaining means so to permit the knob biasing means to move the knob to the extended position for enhanced user access to the knob.

3. The pharmaceutical dispenser of claim 2 wherein the stem drive element is threadably coupled to the stem.

4. The pharmaceutical dispenser of claim 3 wherein the stem drive element is a hollow dose screw having internal threads and the stem has external threads which engage the internal threads of the does screw.

5. The pharmaceutical dispenser of claim 2 wherein the liquid dispensing means includes an accumulator piston, partly defining the accumulator chamber, coupled to an accumulator stem.

6. The pharmaceutical dispenser of claim 2 wherein the liquid dispensing means includes a needle assembly fluidly coupled to the accumulator chamber.

7. The pharmaceutical dispenser of claim 2 further comprising in an axially extending slot formed in one of the telescoping knob and the stem drive element, wherein the telescoping knob is secured to the stem drive element using the axially extending slot and a laterally extending pin extending from the other of the telescoping knob and the stem drive element.

8. The pharmaceutical dispenser of claim 2 wherein the biasing means includes a compression coil spring.

9. The pharmaceutical dispenser of claim 2 wherein the retaining means includes an annular groove formed in the telescoping knob, a trigger mounted to the body and having a tooth portion sized and positioned to engage the annular groove when the telescoping knob is in the collapsed position, and spring means for biasing the tooth portion into engagement with the annular groove.

10. The pharmaceutical dispenser of claim 9, wherein the releasing means includes a user-accessible portion of the trigger, the user-accessible portion sized and positioned to permit the user to move the tooth out of engagement with the annular groove.

11. A pharmaceutical dispenser comprising:
at least two pharmaceutical cartridges each having a barrel, the barrel having a cartridge interior, an open end and an accessible end, a piston within the barrel and a liquid within the cartridge interior between the piston and the accessible end;
a body configured to house the cartridges therein;
an accumulator/dispensing assembly mounted to the body and including an accumulator chamber fluidly coupled to the cartridge interiors;
a piston driver for each said cartridge mounted to the body, the piston drivers each including a stem driver having a longitudinal axis and a stem, the stem driver including a rotatable dose screw, the stem having a proximal end and a distal end which engages the piston, the dose screw drivingly coupled to the stem so that rotary movement of the dose screw determines the amount of axial movement which is applied to the stem, and thus the piston, by the does screw so to determine how much of the liquid within the cartridge interior is forced into the accumulator chamber;
the accumulator/dispensing assembly including means for dispensing liquid from the accumulator chamber;
the dose screw having external dose indicator threads; and
a dose indicator assembly, which indicates to the user the amount of each liquid is driven from the cartridges to the accumulator through the rotation of the dose screw, including:
a frame movably mounted to the body;
a follower, for each cartridge, slidably mounted to the frame, the follower having teeth which engage the dose indicator threads;
a dose indicator, secured to each of the followers, movable along the frame so that as the dose screw rotates, the follower and dose indicator secured thereto move according to the rotary motion of the dose screw;
means for biasing the dose indicator device towards a start position; and
frame lifter means for moving the frame away from the dose screws so to disengage the followers from the external indicator threads allowing the dose indicator biasing means to move the indicators to the start position.

12. The pharmaceutical dispenser of claim 11 wherein the liquid dispensing means includes a needle assembly fluidly coupled to the accumulator chamber.

13. The pharmaceutical dispenser of claim 11 wherein the liquid dispensing means includes an accumulator piston, partly defining the accumulator chamber, and an accumulator stem coupled to said piston.

14. The pharmaceutical dispenser of claim 13 wherein the frame lifter includes a cam surface on the accumulator stem and a cam follower, mounted within the body, having a cam contact portion engagable with the cam surface and a frame contact portion engagable with the frame, the frame contact engaging the frame and biasing the frame away from the system drivers when the cam contact portion engages the cam surface.

15. The pharmaceutical dispenser of claim 14 wherein the accumulator stem is configured to move in the distal direction during a delivery stroke and the liquid dispensing means includes a spring configured so that the user may continue to move the accumulator stem in the distal direction after dispensing the liquid from the accumulator chamber at the end of the delivery stroke.

16. The pharmaceutical dispenser of claim 15 wherein the cam contact portion of the cam follower is positioned in an axially extending recess so that the cam contact portion does not contact the cam surface on the accumulator stem until after the end of the delivery stroke.

17. The pharmaceutical dispenser of claim 11 wherein the frame lifter includes means for moving at least a portion of the frame away from the dose screws after the liquid dispensing means has dispensed the liquid from the accumulator chamber.

18. The pharmaceutical dispenser of claim 11 wherein the frame is pivotably mounted to the body.

19. The pharmaceutical dispenser of claim 11 wherein the dose indicator includes a continuous loop of flexible material.

20. The pharmaceutical dispenser of claim 19 wherein the dose indicator includes a line of demarcation on the loop of flexible material.

21. The pharmaceutical dispenser of claim 11 wherein the dose indicator biasing means includes an elastic member connected to the follower and to the frame.

22. A pharmaceutical dispenser comprising:
first and second pharmaceutical cartridges each having a barrel, the barrel having a cartridge interior, an open end and an accessible end, a piston within the barrel and a liquid within the cartridge interior between the piston and the accessible end;
a body;
a manifold/cartridge/accumulator assembly, removably mountable to the body to a fully inserted position, comprising:
a manifold assembly to which the first and second cartridges are removably mounted;
an accumulator/dispensing assembly secured to the manifold assembly and including an accumulator chamber; and
the manifold assembly including a fluid pathway fluidly coupling the cartridge interiors to the accumulator chamber;

a piston driver for each said cartridge mounted to the body, the piston drivers each including a locking collar element, a movable stem driver and an axially movable stem, the stem driver including a stem drive element, the stem having a proximal end and a distal end which engages the piston;

means for automatically drivingly coupling the stem drive element to the stem only after the manifold/cartridge/ accumulator assembly is in the fully installed position, whereby movement of the stem drive element determines the amount of axial movement which is applied to the stem, and thus the piston, by the stem drive element so to determine how much of the liquid within the cartridge interior is forced into the accumulator chamber; and the accumulator/dispensing assembly including means for dispensing liquid from the accumulator chamber.

23. The pharmaceutical dispenser of claim 22 wherein the body includes an open distal end, the manifold/cartridge/accumulator assembly being slidably mountable to the body through said open distal end so that the manifold/cartridge/accumulator assembly is in the fully installed position.

24. The pharmaceutical dispenser of claim 22 wherein the manifold assembly includes hollow spikes which pierce the first and second cartridges when the cartridges are mounted thereto.

25. The pharmaceutical dispenser of claim 22 further comprising means of presenting fluid flow from the fluid pathway into either of the first or second cartridges.

26. The pharmaceutical dispenser of claim 22 further comprising threads, wherein the stem drive element is a rotatable stem drive element drivingly coupled to the stem by the threads.

27. The pharmaceutical dispenser of claim 26 wherein:
the stem has a length and includes external threads along a portion of the length; and
the stem drive element is hollow and has internal threads which engage the external threads when the automatically drivingly coupling means drivingly couples the stem drive element to the stem.

28. A pharmaceutical dispenser comprising:
at least two pharmaceutical cartridges each having a barrel, the barrel having a cartridge interior, an open end and an accessible end, a piston within the barrel and a liquid within the cartridge interior between the piston and the accessible end;
a body configured to house the cartridges therein;
an accumulator/dispensing assembly mounted to the body and including an accumulator chamber fluidly coupled to the cartridge interiors;
a piston driver for each said cartridge mounted to the body, the piston drivers each including a movable stem driver and a stem, the stem driver including a stem drive element, the stem having a proximal end and a distal end which engages the piston, the stem drive element drivingly coupled to the stem so that movement of the stem drive element determines the amount of axial movement which is applied to the stem, and thus the piston, by the stem drive element so to determine how much of the liquid within the cartridge interior is forced into the accumulator chamber; and
the accumulator/dispensing assembly including means for dispensing liquid from the accumulator chamber.

* * * * *